US005858369A

United States Patent [19]

Matsuo et al.

[11] Patent Number: 5,858,369

[45] Date of Patent: Jan. 12, 1999

[54] ANTI-ACIDS SECRETORY RECOMBINANT BCG VACCINE

[75] Inventors: Kazuhiro Matsuo; Yoshitomo Chujo; Akihiro Yamazaki, all of Kawasaki; Mitsuo Honda, Mitaka; Shudo Yamazaki, Higashiyamato; Hiromichi Tasaka, Kure, all of Japan

[73] Assignees: Ajinomoto Co., Inc.; Japan as represented by Director General of Agency of National Institute of Health, both of Tokyo, Japan

[21] Appl. No.: 975,699

[22] Filed: Nov. 21, 1997

Related U.S. Application Data

[63] Continuation of Ser. No. 619,512, Mar. 29, 1996, abandoned.

[30] Foreign Application Priority Data

Jul. 29, 1994 [JP] Japan .................................... 6-178462

[51] Int. Cl.$^6$ .......................... A61K 39/00; A61K 39/02; A61K 38/00; C07H 21/04

[52] U.S. Cl. .................................... 424/192.1; 424/200.1; 424/208.1; 424/248.1; 536/23.4; 536/23.72; 530/326; 530/327

[58] Field of Search ............................. 424/192.1, 200.1, 424/208.1, 248.1; 536/23.4, 23.72; 530/326, 327

*Primary Examiner*—Jeffrey Stucker
*Assistant Examiner*—Hankyel T. Park
*Attorney, Agent, or Firm*—Oblon, Spivak, McClelland, Maier & Neustadt, P.C.

[57] ABSTRACT

A vaccine containing *Mycobacterium bovis* BCG which secretes a fusion protein to be obtained by inserting a foreign antigen peptide into the molecular surface of a secretory protein, a carrier, having a signal peptide. BCG constituting the present invention secretes a fusion protein to be obtained by inserting a foreign antigen peptide into the molecular surface of an α-antigen derived from mycobacteria. Said fusion protein has significantly increased antigenicity and immunogenicity. Therefore, when it is inoculated into animals, it is efficiently recognized by B cells which recognize said antigen, thereby effectively inducing the production of an antibody to said antigen. When said BCG itself is inoculated into animals, it continuously secretes said fusion protein in the bodies of the animals while continuously propagating therein. Therefore, said BCG is an extremely useful vaccine.

16 Claims, 11 Drawing Sheets lanes 1, 4:EQ192/pUR289
2, 5:EQ192/pUR289+α-Leu38-Ala57
3, 6:EQ192/pUR289+α-Ser184-Asn203 lanes 1, 4: *M. smegmatis*/pIJK-1
2: *M. smegmatis*/pIJK-V3 (HTLVIIIB-XhoI)
3: *M. smegmatis*/pIJK-V3 (HTLVIIIB-PstI)
5: *M. smegmatis*/pIJK-V3 (HIV Japanese-XhoI)
6: BCG/pIJK-1
7: BCG/pIJK-V3 (HIV Japanese-XhoI)

FIG. 4A
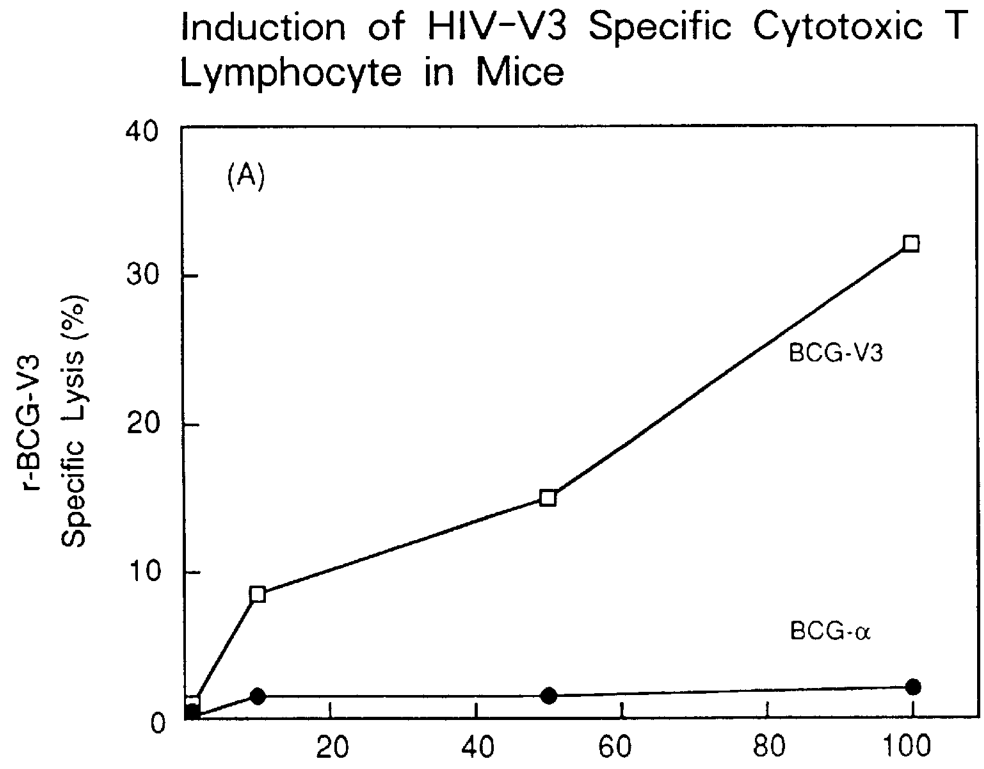
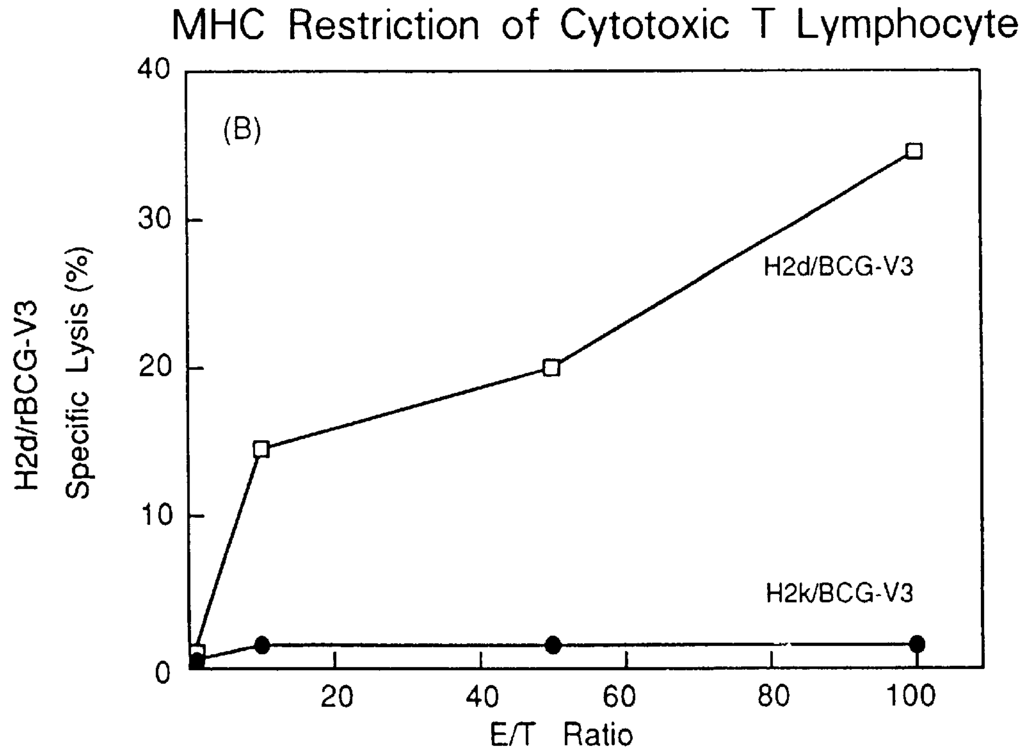
FIG. 4B

FIG. 5A
Neutralization of clinical isolate by guinea pig antibody (5mg subcutaneous inoculation)
A V3 sequences of clinical isolate
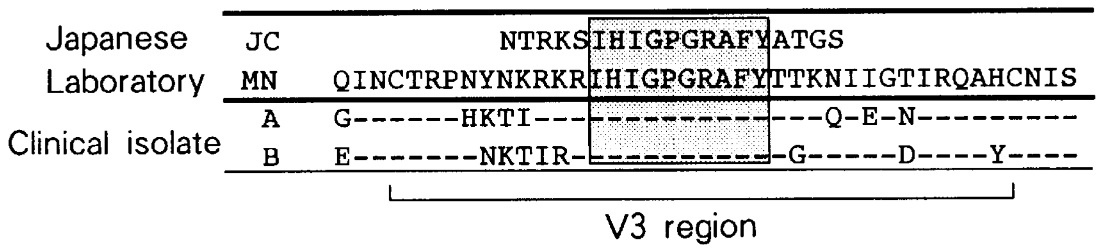
B in vitro neutralizing activity
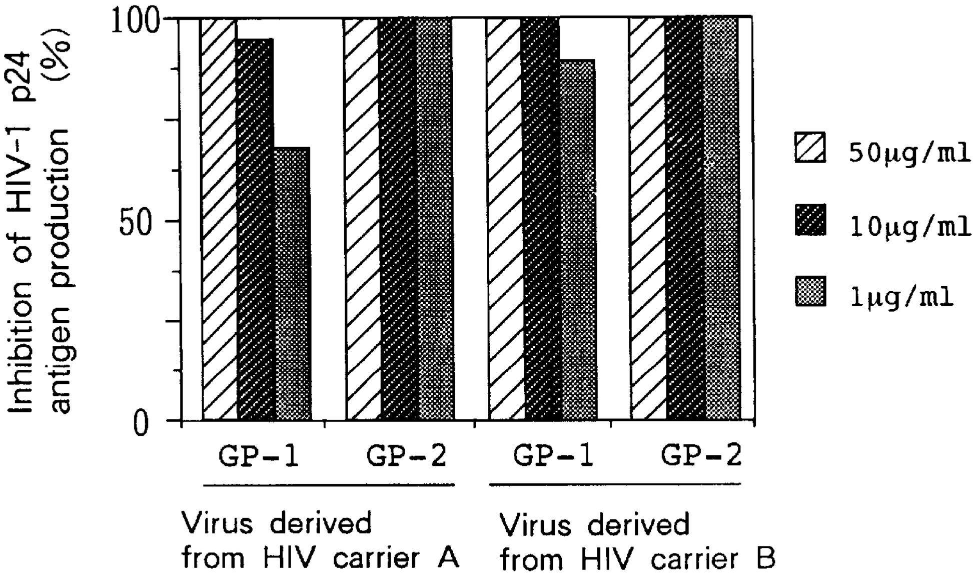
FIG. 5B FIG. 6A
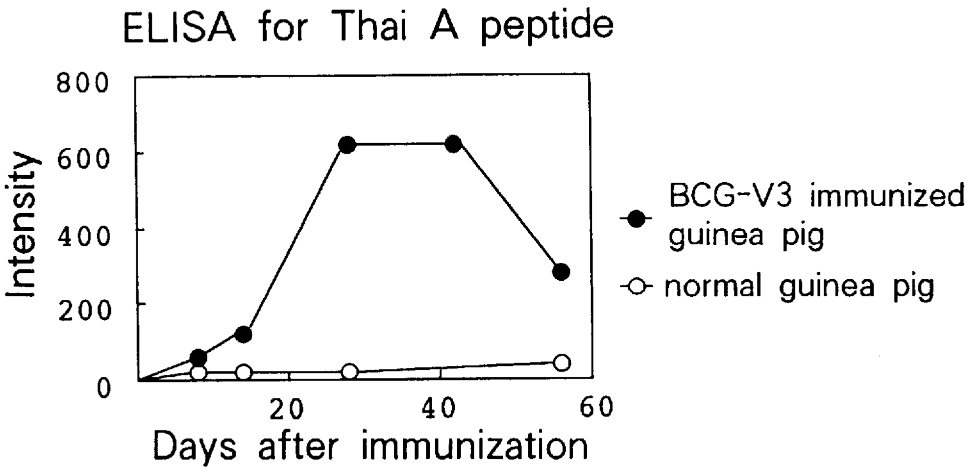
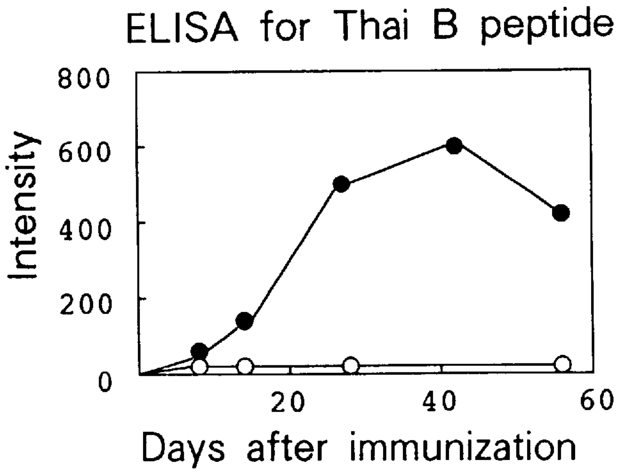
FIG. 6B Time course with time of anti-V3 antibody in BCG-V3 immunized monkeys Production of neutralizing antibody MN strain neutralizing activity 4 weeks after BCG-V3 immunization (in vitro)

Construction of HIV-1-SIVmac chimera virus gene having HIV Japanese V3 consensus squence lanes 1 : BCG-α
2 : BCG-gp41-X6
3 : BCG-gp41-X13

ANTI-ACIDS SECRETORY RECOMBINANT BCG VACCINE

This application is a Continuation of application Ser. No. 08/619,512, filed on Mar. 29, 1996, now abandoned; which was filed as International Application No. PCT/JP95/01515, filed on Jul. 31, 1995.

FIELD OF THE INVENTION

The present invention relates to a vaccine containing *Mycobacterium bovis* BCG (hereinafter which may be referred to as BCG) which secretes a fusion protein to be obtained by inserting a foreign antigen peptide into the molecular surface of a secretory protein, a carrier, having a signal peptide. Concretely, the secretory peptide, a carrier, having a signal peptide is the α-antigen derived from mycobacteria, and the foreign antigen peptide is an antigen peptide of a human immunodeficiency virus type 1 (HIV-1) surface antigen.

PRIOR ART

An attempt to improve BCG by means of recombinant DNA technology to thereby utilize it as a vaccine against various pathogens has been started since 1988 when the transformation system of BCG was established (see Proc. Natl. Acad. Sci., USA, 85, 6987 (1988)).

BCG is an attenuated strain of bovine tubercle bacillus, and this is only one live vaccine which has been accepted to be applicable to human beings. This is characterized in that it has low toxicity and is safe, it has a high adjuvant activity, its effect lasts long, it is low-priced, it is resistant to heat and its peroral administration is possible. Therefore, it has been expected that, if BCG may be artificially improved to express an antigen, namely, a foreign antigen against various pathogenic bacteria and viruses, such will be a pioneer in the development of extremely effective vaccines.

Meanwhile, a BCG system capable of secreting and expressing an intended foreign antigen has been established (see Infect. Immun., 58, 4049 (1990)), and the application of the system to vaccines has been expected. In fact, mycobacteria capable of expressing and secreting a fusion protein to be obtained by fusing the α-antigen derived from *Mycobacterium kansasii,* as a carrier, and the antigenic site (comprising 9 amino acids) of gag p17 of HIV-1 have been developed (see Infect. Immun., 58, 4049 (1990)). In addition, the expression and secretion of a peptide composed of 15 amino acid residues in the third variable region (hereinafter referred to as V3 region or V3 epitope) existing in the surface antigen which is said to be one of protective antigens against infection with HIV-1 has been succeeded in (see Vaccine, 12, 153 (1994)). The peptide composed of 15 amino acid residues in said V3 region has both cytotoxic T cell epitope and B cell epitope. To express the peptide, the α-antigen derived from *M. kansasii* has been used as a carrier protein, and the foreign antigen peptide is fused to the α-antigen at the position near its C-terminal. In other words, the mycobacteria secrete the fusion protein.

However, when BCG capable of secreting the fusion protein composed of the peptide comprising the 15 amino acid residues in the V3 region and the α-antigen derived from *M. kansasii* were inoculated into mice, the level in the production of the antibody in the mice was not so high as expected though cytotoxic T cells were noticeably induced.

Apart from BCG, studies of developing vaccines using virus vectors are being promoted in these days. For instance, various carrier proteins such as the surface protein hemagglutinin of influenza virus (see J. Virol., 67, 6659 (1993)) and the surface protein VP-1 of poliovirus (see J. Virol., 66, 3161 (1992)) are fused with V3 epitope to design fusion proteins, and these viruses are modified with the recombinant DNA so as to be able to express the fusion proteins on the viruses. There are some reports demonstrating the immunization of animals with the thus-obtained chimera viruses. It has been known that the animals immunized with these chimera viruses may efficiently produce the antibody against V3 epitope.

The higher-order structures of the carrier proteins derived from the above-mentioned viruses have already been clarified. In the above-mentioned fusion proteins, the foreign antigen peptide has been inserted into the loop site which may become B cell epitope with ease and which exists on the molecular surface of the carrier protein.

DISCLOSURE OF THE INVENTION

An object of the present invention is to provide a vaccine containing *Mycobacterium bovis* BCG which secretes a fusion protein to be obtained by inserting a foreign antigen peptide into the molecular surface of a secretory protein, a carrier, having a signal peptide. Another object of the present invention is to make said BCG usable as a vaccine, more concretely, to prepare BCG capable of expressing and secreting a fusion protein to be obtained by fusing a secretory protein, a carrier, having a signal peptide and a foreign antigen peptide, and to modify said fusion protein so that it may be recognized by cytotoxic T cells as an epitope and may be recognized by B cells as an epitope and, as a result, it may efficiently induce cytotoxic T cells and it may significantly increase the level in the production of antibodies.

When BCG capable of secreting the fusion protein composed of the peptide comprising the 15 amino acid residues in the V3 region and the α-antigen derived from *M. kansasii* was inoculated into mice, the level in the production of the antibody in the mice was not so high as expected, though cytotoxic T cells were significantly induced, as so mentioned hereinabove.

It has already been clarified that the antibody against the V3 region protects against the HIV-1 infection in chimpanzee (see Nature 345, 622 (1990)). Therefore, it is the major stream to use a protein which can be expected to induce the production of antibody against the V3 region as an effective vaccine component in recent developments of AIDS vaccines. Concretely, there may be mentioned, for instance, the surface antigen gp120 containing the V3 region, which is produced in animal cells or insect cells modified by gene recombinant technology and is used as a vaccine. However, the effect of the vaccine was very weak.

Both the attempts were intended to have the antigen induce remarkable production of an antibody against the V3 region, which antibody could have activity to inhibit the propagation of HIV-1 and to protect against the infection. However, so far it has not been successful to obtain sufficient effects. Accordingly, it is highly expected that if an antigen capable of inducing remarkable production of an antibody which has activity to inhibit the propagation of HIV-1 and to protect against the infection is created, such an antigen would be very useful as a vaccine.

We, the present inventors considered that even if the peptide comprising the 15 amino acid residues in the V3 region is fused to the C-terminal position of the α-antigen derived from *M. kansasii,* the V3 epitope will hardly have its native conformation generally appearing on HIV-1 surface antigen so that said epitope will hardly be recognized by B cells. Considering so, we, the present inventors prepared BCG capable of secreting a fusion protein to be obtained by inserting a foreign antigen peptide into the molecular surface of a secretory protein, a carrier, having a signal peptide and considered to use it as a vaccine.

For this, a carrier protein which is derived from mycobacteria and whose higher-order structure has been known is needed. However, none of proteins derived from mycobacteria, including the α-antigen used in the present invention, has been analyzed to clarify their higher-order structures.

We, the present inventors have clarified that, when a foreign antigen peptide is expressed and secreted, using the α-antigen derived from mycobacteria as a carrier, the fusion shall be effected at what position in the α-antigen so as to realize the highest antigenicity and thus have succeeded in the development of a vaccine capable of inducing significant production of the antibody against said foreign antigen. As a result, we, the present inventors have completed the present invention. More precisely, we presumed and determined a B cell epitope (antigen determinant group) of the α-antigen itself located in the hydrophilic region which is foreseen from the amino acid sequence of the α-antigen derived from *M. kansasii* and inserted a foreign antigen peptide into the vicinity of the thus-determined region, by which we have succeeded in making BCG secrete the fusion protein having a high antigenicity and have also succeeded in the development of a vaccine capable of inducing significant antibody production.

The present invention provides a vaccine containing *Mycobacterium bovis* BCG which secretes a fusion protein to be obtained by inserting a foreign antigen peptide into the molecular surface of a secretory protein, a carrier, having a signal peptide.

Examples of the secretory protein, a carrier, having a signal peptide include an α-antigen derived from mycobacteria. Preferable vaccines of the invention include a vaccine containing *Mycobacterium bovis* BCG which secretes a fusion protein to be obtained by inserting a foreign antigen peptide between the 184th Ser residue and the 185th Asp residue in said α-antigen.

Examples of the foreign antigen peptide include an antigen peptide of HIV-1 surface antigen, in particular an antigen peptide comprising the third variable region of HIV-1.

Particularly preferred vaccine of the invention is a vaccine containing *Mycobacterium bovis* BCG in which the antigen peptide of HIV-1 surface antigen is an antigen peptide comprising the third variable region composed of 19 amino acid residues of Asn Thr Arg Lys Ser Ile His Ile Gly Pro Gly Arg Ala Phe Tyr Ala Thr Gly Ser (SEQ ID NO: 1), in particular a vaccine for curing and preventing AIDS.

Another particularly preferred vaccine of the invention is a vaccine containing *Mycobacterium bovis* BCG in which the antigen peptide of HIV-1 surface antigen is an antigen peptide composed of 13 amino acid residues of Lys Asn Glu Gln Glu Leu Leu Glu Leu Asp Lys Trp Ala (SEQ ID NO: 13) derived from gp41, in particular a vaccine for curing and preventing AIDS.

Still other particularly preferred vaccine of the invention is a vaccine containing *Mycobacterium bovis* BCG in which the antigen peptide of HIV-1 surface antigen is an antigen peptide composed of 18 or 19 amino acid residues as described below, in particular a vaccine for curing and preventing AIDS.

Asn Thr Arg Lys Ser Val His Ile Gly Pro Gly Gln Ala Phe Tyr Ala Thr Gly Asp (SEQ ID NO: 14) (Subtype A: West and Central Africa)

Asn Thr Arg Lys Ser Ile His Ile Gly Pro Gly Arg Ala Phe Tyr Thr Thr Gly Glu (SEQ ID NO: 15) (Subtype B: North and South America, Europe and Asia)

Asn Thr Arg Lys Ser Ile Arg Ile Gly Pro Gly Gln Thr Phe Tyr Ala Thr Gly Glu (SEQ ID NO: 16) (Subtype C: South and Central Africa)

Asn Thr Arg Gln Arg Thr His Ile Gly Pro Gly Gln Ala Leu Tyr Thr Thr Arg (SEQ ID NO: 17) (Subtype D: Central Africa)

Asn Thr Arg Thr Ser Ile Thr Ile Gly Pro Gly Gln Val Phe Tyr Arg Thr Gly Asp (SEQ ID NO: 18) (Subtype E: Thai and Central Africa)

The lanes 1 and 4 show the results of the electrophoresis of the cell extracts obtained from *Escherichia coli* EQ192 (EQ192/pUR298) which carries plasmid pUR298 to express β-galactosidase. The lanes 2 and 5 show the results of the electrophoresis of the cell extracts obtained from *Escherichia coli* EQ192 (EQ192/pUR289+α-Leu38-Ala57) which carries plasmid pUR289+α-Leu38-Ala57 to express the fusion protein composed of β-galactosidase and the peptide having the sequence from the 38th Leu residue to the 57th Ala residue in the α-antigen. The lanes 3 and 6 show the results of the electrophoresis of the cell extracts obtained from *Escherichia coli* EQ192 (EQ192/pUR289+α-Ser184-Asn203) which carries plasmid pUR289+α-Ser184-Asn203 to express the fusion protein composed of β-galactosidase and the peptide having the sequence from the 184th Ser residue to the 203th Asn residue in the α-antigen.

The arrow indicates the position corresponding to β-galactosidase-fusion protein having molecular weight of about 120,000.

Figure 2:
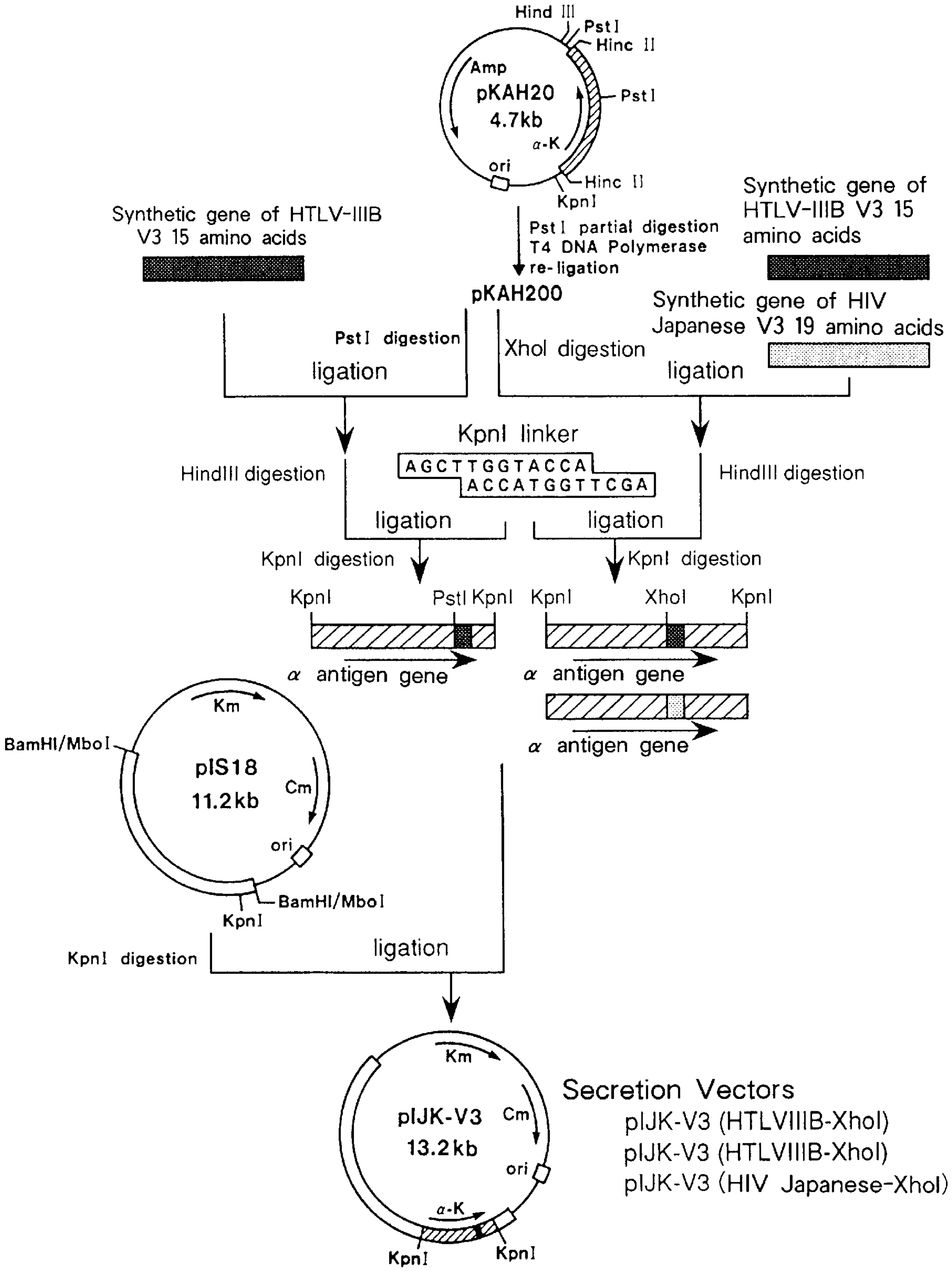

FIG. 2 shows a strategy for the construction of the vector expressing and secreting the fusion protein composed of the α-antigen and V3 epitope of HIV-1. The blocks with slanting lines indicate the DNA fragment containing the α-antigen derived from *Mycobacterium kansasii* (in the figure, referred to as α-K); the white blocks indicate the DNA fragment containing replication-initiating region of the plasmid of mycobacteria; the blocks with dark dots indicate the synthetic gene composed of the 15 amino acids of the HTLVIIIB V3 epitope; and the blocks with light dots indicate the synthetic gene composed of the 19 amino acids of the HIV(Japanese) V3 epitope. Amp, Km and Cm represent genes resistant to ampicillin, kanamycin and chloramphenicol, respectively. pIJK-V3(HTLVIIIB-PstI) and pIJK-V3(HTLVIIIB-XhoI) represent plasmids pIJK-V3 containing the V3 epitope derived from HTLVIIIB strain into the PstI and the XhoI sites, respectively. pIJK-V3(HIV Japanese-XhoI) represents a plasmid pIJK-V3 containing the V3 epitope of the HIV Japanese consensus sequence into the XhoI site.

Figure 3:
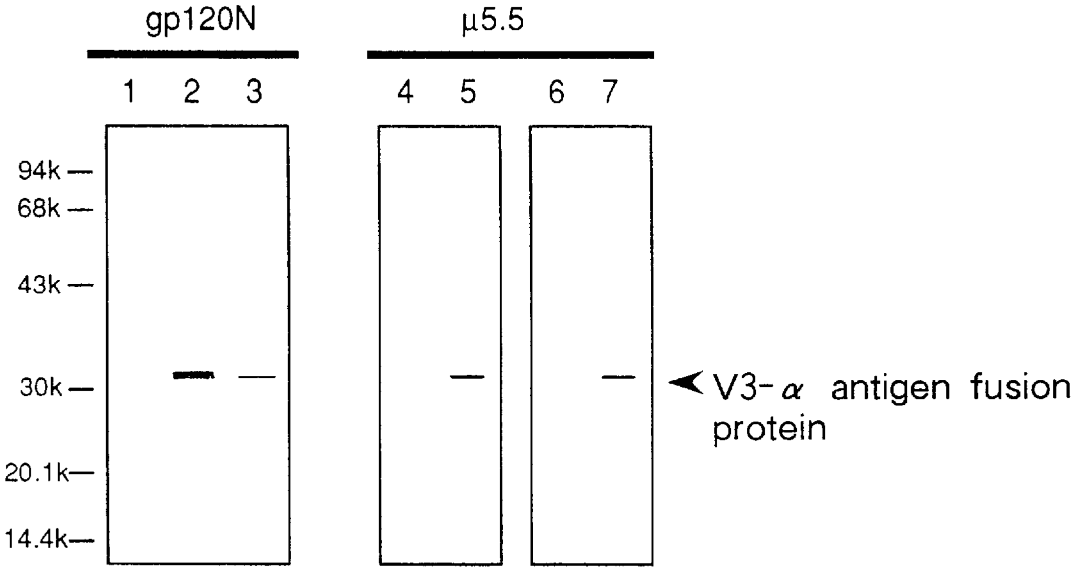

FIG. 3 shows the results of the western blotting analyses of the proteins in the culture supernatant of *Mycobacterium smegmatis* and BCG each carrying a recombinant secretory vector.

The lane 1 shows the result for control supernatant from the culture of *Mycobacterium smegmatis* carrying pIJK-1.

The lane 2 shows the result of the supernatant from the culture of *Mycobacterium smegmatis* carrying pIJK-V3 (HTLVIIIB-XhoI). This is to check the antigen-antibody reaction of the fusion protein formed by fusing the peptide composed of the HTLVIIIB-derived 15 amino acid residues to the position of the 184th Ser residue in the α-antigen.

The lane 3 shows the result of the supernatant from the culture of *Mycobacterium smegmatis* carrying pIJK-V3 (HTLVIIIB-PstI). This is to check the antigen-antibody reaction of the fusion protein formed by fusing the peptide composed of the HTLVIIIB-derived 15 amino acid residues to the position of the 280th Gln residue in the α-antigen.

The lane 4 is the same as the lane 1.

The lane 5 shows the result of the supernatant from the culture of *Mycobacterium smegmatis* carrying pIJK-V3 (Japanese-XhoI). This is to check the antigen-antibody reaction of the fusion protein formed by fusing the peptide composed of the Japanese strain-derived 19 amino acid residues to the position of the 184th Ser residue in the α-antigen.

The lane 6 shows the result for control supernatant from the culture of *Mycobacterium bovis* BCG carrying pIJK-1.

The lane 7 shows the result of the supernatant from the culture of *Mycobacterium bovis* BCG carrying pIJK-V3 (Japanese-XhoI). This is to check the antigen-antibody reaction of the fusion protein formed by fusing the peptide composed of the Japanese strain-derived 19 amino acid residues to the position of the 184th Ser residue in the α-antigen.

To label the lanes 1, 2 and 3, used was a neutralizing monoclonal antibody gp120N which recognizes the V3 epitope of HIV-1 HTLVIIIB.

To label the lanes 4, 5, 6 and 7, used was a neutralizing monoclonal antibody μ 5.5 which recognizes the V3 epitope of the consensus sequence of HIV-1(Japan).

The bands each indicating the fusion protein are found at the position of a molecular weight of about 32,000.

FIG. 4 shows the results of CTL induction in mice. (A) shows induction of HIV-V3 specific cytotoxic T lymphocyte in mice. (B) shows MHC restriction of cytotoxic T lymphocyte. The axis of abscissas indicates the ratio of the effector cells to the target cells and the axis of ordinates indicates the proportion of the target cells which were subjected to specific lysis by cytotoxic T cells. BCG-α (A) shows the results from the immunization with BCG expressing only the α-antigen, and BCG-V3 (B) shows the results from the immunization with BCG expressing the V3 epitope. H2d/BCG-V3 shows the results obtained using P815 cells as the target cells, and H2k/BCG-V3 shows the results obtained using SW5147 cells as the target cells.

FIG. 5 shows the results of neutralization assay of clinically isolated viruses using antibodies produced in guinea pigs. (A) indicates the amino acid sequences of the V3 regions of the viruses which were isolated from two Japanese HIV carriers and used in the assay. The shadowed area indicates the neutralizing epitope regions. (B) indicates the results of the in vitro neutralization assay which are expressed by the inhibition ratio. GP-1 and GP-2 show the results obtaioned by the use of serum immunoglobulin of Groups 1 and 2 each containing 20 guinea pigs. The black bars, the bars with slanting lines and the bars with dots show the results obtained when the immunoglobulin was added to the assay system in the concentration of 50, 10 and 1 μg/ml, respectively. The axis of abscissas shows a ratio of the decrease in the amount of p24 antigen (infection inhibition) observed in the culture supernatant when the antibody was added as compared with the amount of p24 antigen (control) observed when the antibody was not added.

FIG. 6 shows the results of cross reactivity with Thai A (A) and Thai B (B) V3 peptides determined by ELISA method (A) shows ELISA for Thai A peptide. (B) shows ELISA for Thai B peptide. The black dots show the results obtained by the sera of guinea pigs immunized by BCG-V3 and the white dots show the results obtained by the sera of normal guinea pigs not immunized by BCG. The axis of abscissas shows the absorbance intensity at 414 nm of p-nitrophenol, a coloring agent for the ELISA.

Figure 7:
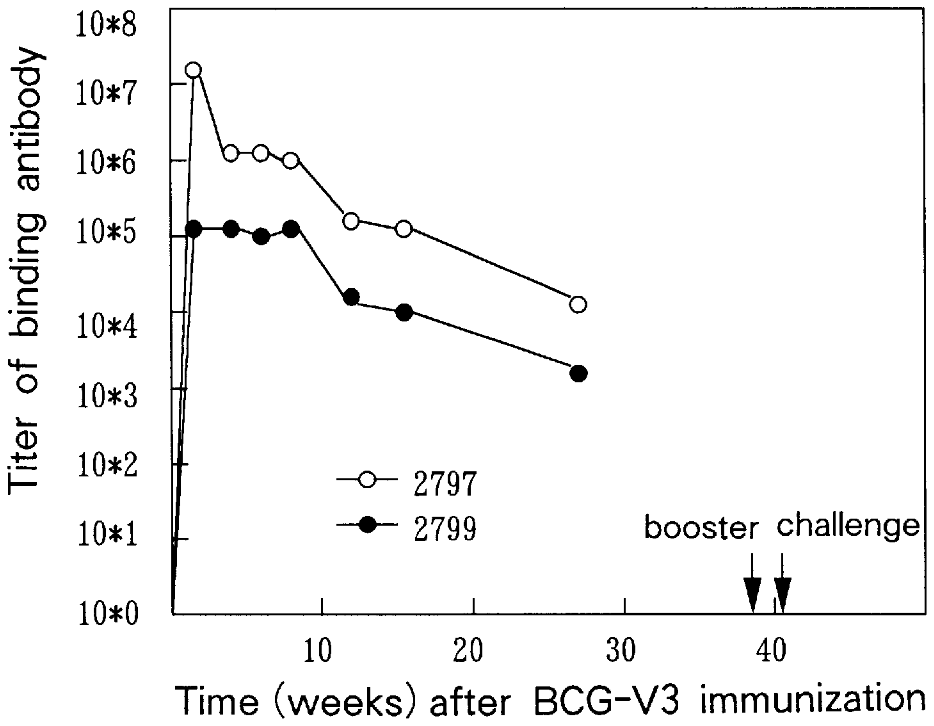

FIG. 7 shows the change with time in the level of the anti-V3 antibody in two cynomolgus monkeys immunized with BCG-V3. The white dots and the black dots represent the results of animals #2797 and #2799, respectively and the axis of abscissas represents binding antibody titer. 10*8 means $10^8$.

Figure 8:
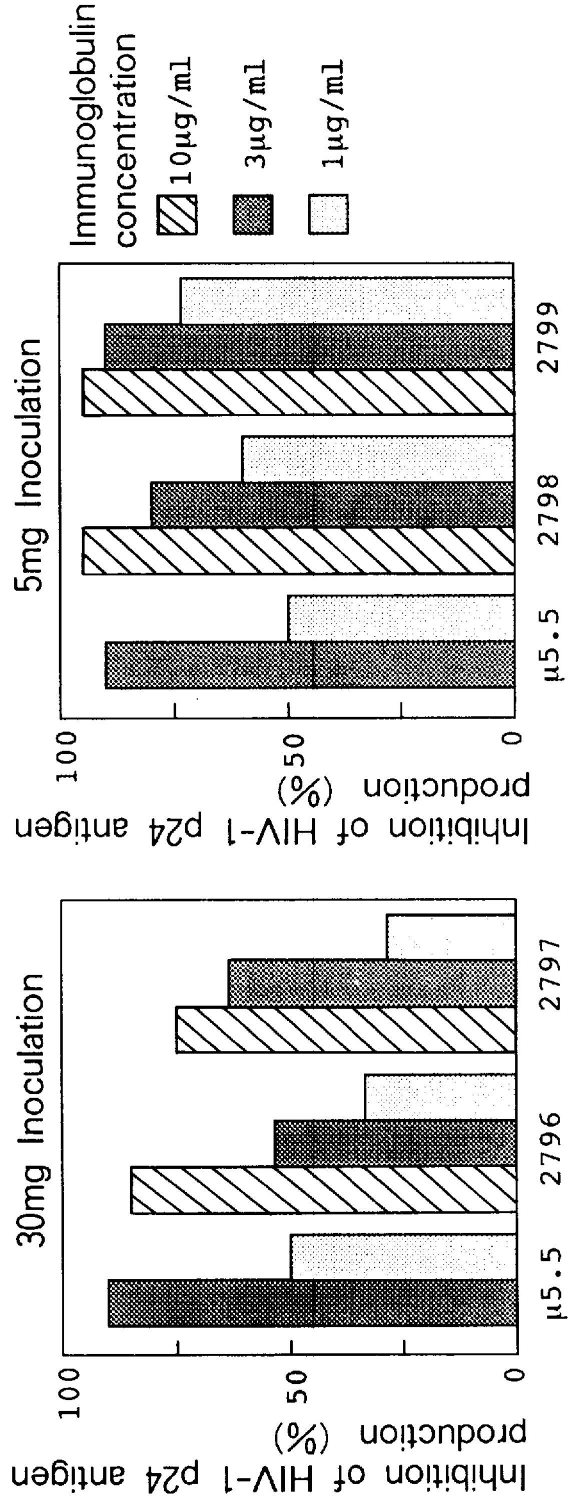

FIG. 8 shows the results of the neutralization assay of HIV-1 MN strain using serum antibody of cynomolgus monkeys four weeks after immunized with BCG-V3. (A) shows MN strain neutralizing activity four weeks after BCG-V3 immunization with a 30 mg inoculation. (B) shows MN strain neutralizing activity four weeks after BCG-V3 immunization with a 5 mg inoculation. Animals #2796 and #2797 were immunized with 30 mg of BCG-V3 and animals #2798 and #2799 were immunized with 5 mg of BCG-V3. The black bars, the bars with dark dots and the bars with light dots show the results obtained when the immunoglobulin was added to the assay system in the concentration of 10, 3 and 1 μg/ml, respectively. μ 5.5 is a neutralizing monoclonal antibody used as a positive control. The axis of abscissas shows the inhibition ratio of HIV-1 p24 antigen production as in Example 5.

Figure 9:
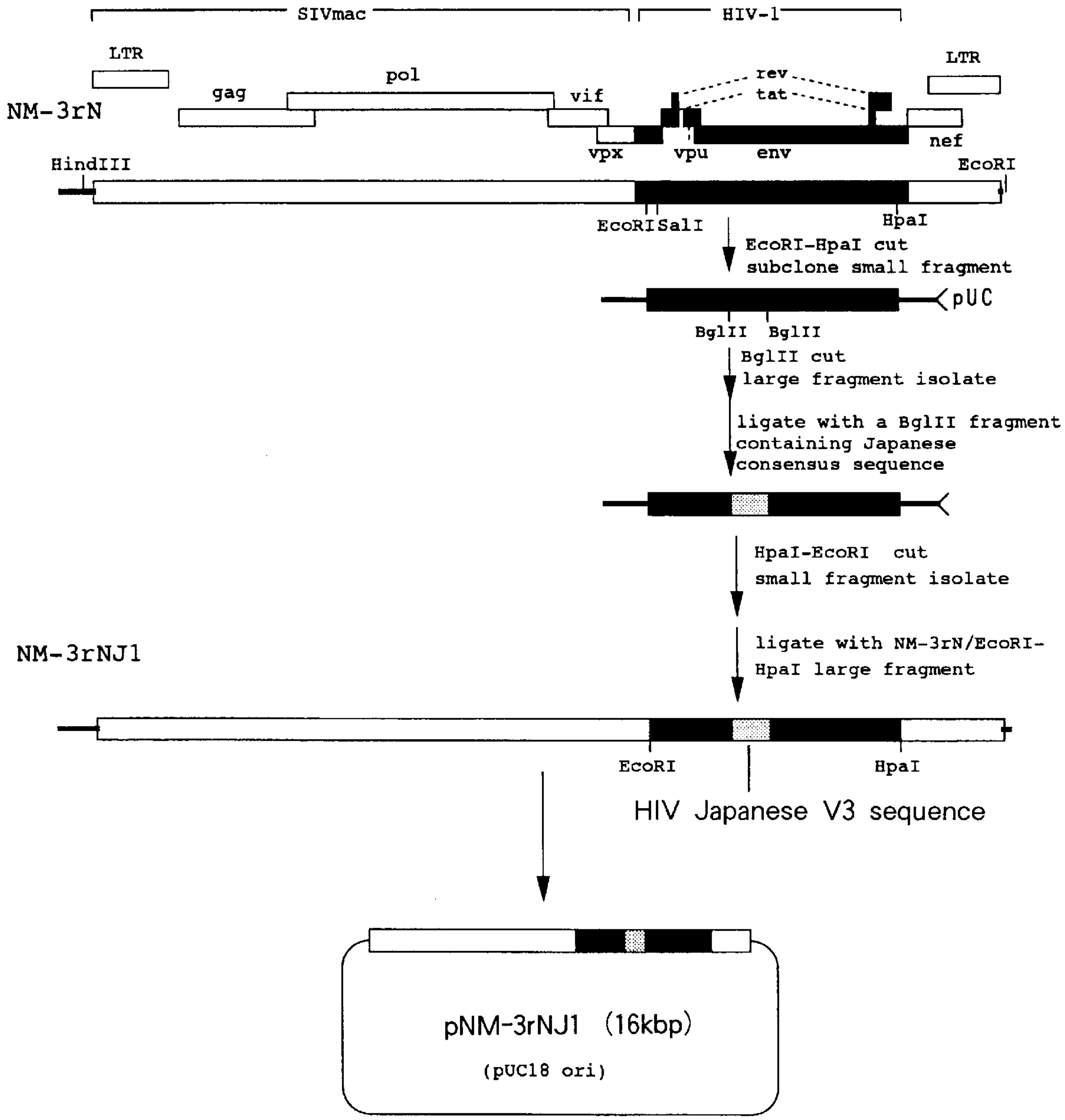

FIG. 9 shows the outline of the construction of HIV-1-SIV chimera virus, NM-3rNJ1 having the consensus sequence of Japanese strain V3. The white bars, the black bars and the bars with light dots show the DNA derived from SIVmac (Simian immunodeficiency virus derived from macaca monkey), the DNA derived from HIV-1(HTLVIIIB) and the DNA containing the V3 region of Japanese strain, respectively.

Figure 10:
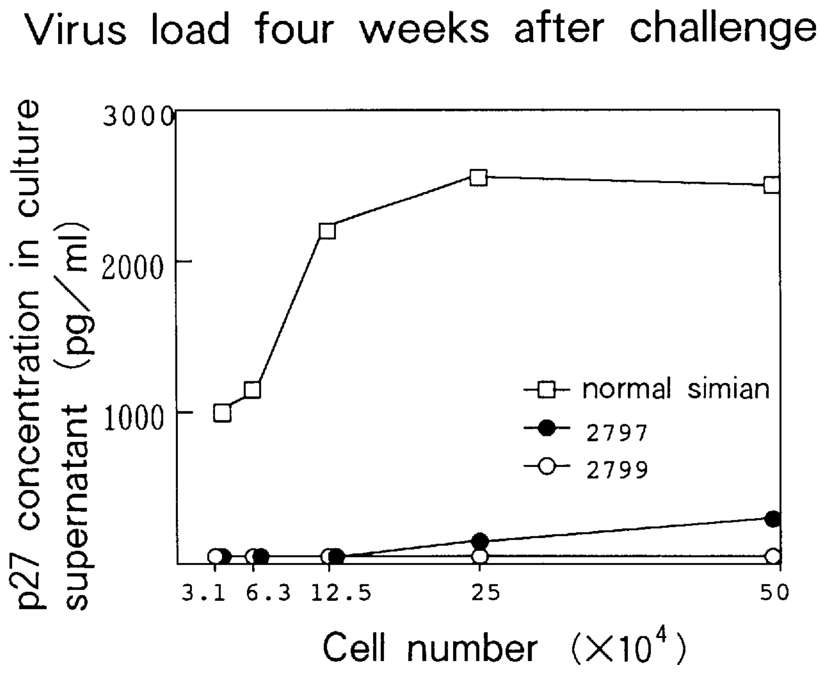

FIG. 10 shows the results of protection from chimera virus infection (virus load) four weeks after the virus challenge. The axis of ordinates indicates the number of simian peripheral blood mononuclear cells used in the co-culture with M8166 cells and the axis of abscissas indicates the amount of the chimera virus expressed by p27 antigen concentration in the culture supernatant at one week after the co-culture. The white squares indicate the results obtained by normal monkey not immunized and the black dots and the white dots indicate the results obtained by the peripheral blood mononuclear cells of #2797 and #2799, respectively.

Figure 11:
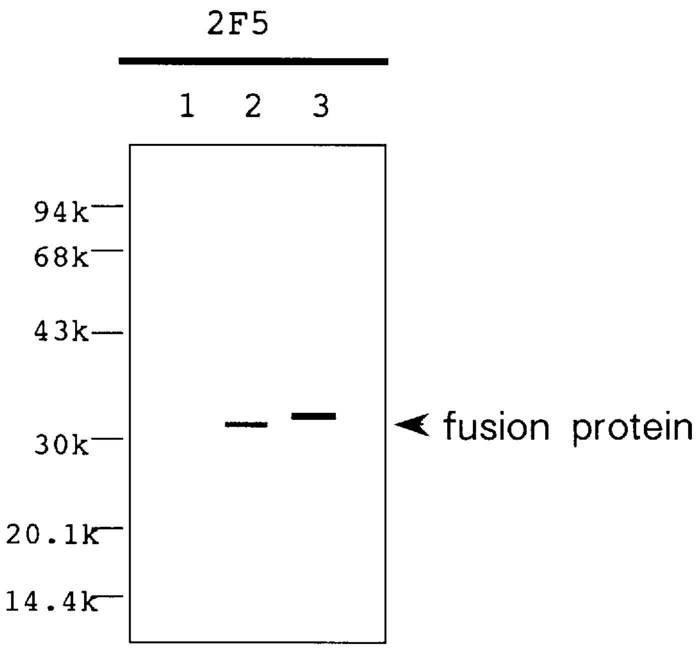

FIG. 11 shows the results of secretion and expression of gp41 neutralizing epitopes (6 amino acids and 13 amino acids) from BCG. The lanes 1, 2 and 3 indicate the results of western blotting analyses after 15% SDS-PAGE fractionation of the proteins in the supernatant from the cultures of BCG-α, BCG-gp41-X6 and BCG-gp41-X13, respectively. To label the lanes, used was the neutralizing monoclonal antibody 2F5 which recognizes HIV-1 gp41.

PREFERRED EMBODIMENTS CARRYING OUT THE INVENTION

The present invention will be explained in detail hereunder.

The secretory protein, a carrier, having a signal peptide constituting the present invention is a protein to be secreted by BCG.

Concretely mentioned is an α-antigen derived from mycobacteria. Especially preferred is an α-antigen derived from *Mycobacterium kansasii* which is used in the examples mentioned hereinafter. Such an α-antigen is a cross-reactive protein, which widely exists also in other mycobacteria. Five α-antigens derived from BCG (see J. Bacteriol., 170, 3847 (1988)), *Mycobacterium kansasii* (see Infect. Immun., 58, 550 (1990)), *Mycobacterium avium* (see Infect. Immun., 61, 1173 (1993)), *Mycobacterium intracellulare* (see Biochem. Biophys. Res. Commun., 196, 1466 (1993)) and *Mycobacterium laprae* (see Mol. Microbiol., 6, 153 (1992)) have heretofore been clarified with respect to their primary structures. All of these have high homology of about 80% in the level of their amino acid sequences. In addition, comparing their hydropathy profiles (hydrophilic-hydrophobic plots), it is known that these are extremely similar. Thus, the positions of the hydrophilic regions appearing on the surfaces of the molecules are conserved among various α-antigens. Therefore, α-antigens derived from various mycobacteria can be used as the carriers.

The method for determining a site located on the molecular surface of the protein is carried out on the basis of the higher-order structure of said protein, if it is clarified. However, it is extremely difficult to completely clarify the higher-order structures of proteins. In fact, therefore, the hydrophilic region of said protein is first determined according to the Hopp and Woods' method (see Proc. Natl. Acad. Sci., USA, 78, 3824 (1981)). Since many hydrophilic amino acid residues exist on the molecular surface of a protein, its hydrophilic region is presumed to be the actual molecular surface region of the protein. Then, it is examined whether the hydrophilic region in fact reacts with an antibody which recognizes the secretory protein. If it reacts, it is demonstrated that the region is the molecular surface region of the protein. Then, a fusion protein is designed so that a foreign antigen peptide may be inserted into said region. To confirm as to whether or not the hydrophilic region corresponds to the region of the actual molecular surface, the thus-designed fusion protein is actually prepared to check its antigenicity while animals are immunized with BCG secreting this. The thus-immunized animals are examined as to whether or not the inserted foreign antigen peptide is recognized by cytotoxic T cells as epitope and is recognized by B cells as epitope with the result that cytotoxic T cells are efficiently induced and the level in the antibody production in the immunized animals is significantly increased.

When an α-antigen derived from *M. kansasii* is used as the secretory protein, a carrier, having a signal peptide, the region in the vicinity of the 184th Ser residue and the 185th Asp residue in said α-antigen is the region of its molecular surface. Therefore, a foreign antigen peptide is inserted between the 184th Ser residue and the 185th Asp residue.

The foreign antigen peptide constituting the present invention is one that is, when applied to animals to immunize them therewith, recognized by cytotoxic T cells as epitope or recognized by B-cells as epitope with the result that it efficiently induces cytotoxic T cells or causes significant increase in the level of the antibody production in the thus-immunized animals. One object of the present invention is to provide a vaccine to be used for curing and preventing bacterial or viral diseases. Therefore, it is preferred that said foreign antigen peptide is a part of the proteins constituting bacteria or viruses causing said diseases. Concretely mentioned are proteins constituting HIV-1. Especially preferred is an antigen peptide of HIV-1 surface antigen. Most preferred is an antigen peptide comprising the third variable region (V3 epitope) composed of 19 amino acids of Asn Thr Arg Lys Ser Ile His Ile Gly Pro Gly Arg Ala Phe Tyr Ala Thr Gly Ser (SEQ ID NO: 1).

An AIDS virus surface antigen gp120 is composed of C1, V1, V2, C2, V3, C3, V4, C4, V5 and C5 in this order from its N-terminal, in which the constant regions (Cs) each having a relatively constant amino acid sequence and the variable regions (Vs) each having a much varied amino acid sequence exist almost alternately. In this, the region between the constant regions C2 and C3 is referred to as the third variable region, and the antigenic site in the third variable region is referred to as V3 epitope. Concretely, this is the region sandwiched between the two 303th and 338th Cys residues in gp120. This region is an extremely variable region, as shown by LaRosa et al. (see Science, 249, 932 (1990)), but it may be a site capable of recognizing an antibody (B cell epitope) that strongly inhibits the growth of viruses in various variants. This antibody is effective in protecting chimpanzees from infection with HIV-1. In addition, since this region contains an epitope of cytotoxic T cells to be recognized by human being having HLA-A2 and A3, it is the best as the foreign antigen peptide for developing an AIDS vaccine capable of producing a neutralizing antibody and inducing cytotoxic T cells.

The gene of V3 epitope may be obtained by the polymerase chain reaction (PCR) method using the primer synthesized on the basis of the base sequence in the C2 and C3 regions (see Science, 230, 1350 (1985)). It may also be obtained by cloning the DNA fragment obtained by the PCR method into a suitable vector to determine its nucleotide sequence followed by chemically synthesizing the DNA on the basis of the thus-determined nucleotide sequence.

Next, a method for producing BCG which secretes a fusion protein to be obtained by inserting a foreign antigen peptide into the molecular surface of a secretory protein, a carrier, having a signal peptide will be explained hereunder. As one means for making BCG express and secrete said fusion protein, mentioned is a method in which a DNA coding for said fusion protein is prepared by recombinant DNA technology and said DNA is introduced into the cells of BCG so that said DNA is stably held in the cells and is expressed by them, by which the fusion protein is secreted.

Next, a method for producing the intended BCG by recombinant DNA technology will be explained hereunder.

In the following explanation, referred to is one example where the secretory protein, a carrier, having a signal peptide is an α-antigen derived from *M. kansasii,* and, as a foreign antigen peptide, an antigen peptide of HIV-1 surface antigen, that is, an antigen peptide comprising the third variable region composed of 19 amino acid residues of Asn Thr Arg Lys Ser Ile His Ile Gly Pro Gly Arg Ala Phe Tyr Ala Thr Gly Ser (SEQ ID NO: 1) is inserted between the 184th Ser residue and the 185th Asp residue in said α-antigen.

In order to make BCG express and secrete a fusion protein to be obtained by inserting a foreign antigen peptide into the hydrophilic region in the α-antigen derived from *M. kansasii,* a synthetic DNA coding for the intended foreign antigen peptide is inserted into an already-known α-antigen secreting vector pIJK-1 (see Infect. Immun., 58, 4049

(1990)) at its suitable restriction enzyme site positioned correspondingly to the hydrophilic region in the α-antigen gene, and the resulting recombinant secretory vector is introduced into BCG.

For instance, utilizing the fact that the DNA corresponding to he 184th Ser residue and the 185th Asp residue, which is one hydrophilic region in the α-antigen, has an XhoI restriction enzyme site, a synthetic DNA coding for the V3 region peptide comprising the 19 amino acid residues, which is an HIV-1 surface antigen, is introduced into the XhoI site of pIJK-1 in accordance with the reading frame of the α-antigen gene, by which a recombinant secretory vector is obtained.

If pIJK-1 is not used, a DNA coding for the α-antigen of *Mycobacterium kansasii* is first prepared. Said DNA is so designed that it may contain a region coding for a signal peptide. To prepare said DNA, the method described in Matsuo et al's report (see Infect. Immun., 58, 550 (1990)) is employed. Next, a plasmid pIS18 that may be stably held in the cells of BCG is prepared. To prepare said plasmid, the method described in Snapper et al's report (see Proc. Natl. Acad. Sci., USA, 85, 6987 (1988)) is employed. Then, the thus-obtained plasmid is digested with a suitable restriction enzyme to make it linear, and this is ligated with said DNA to obtain a recombinant DNA. The position at which said plasmid is cut must be located in the region not necessary for said plasmid to be stably held in the cells of BCG. In order to express said DNA, it is desired that said DNA contains a region that controls the expression of the DNA coding for the α-antigen of *Mycobacterium kansasii,* for example, a promoter. Said recombinant DNA is used as the starting material for constructing a recombinant secretory vector.

To introduce the recombinant secretory vector or the recombinant DNA into BCG, employable is a known electroporation method. The method has been reported by Snapper, et al. (see Proc. Natl. Acad. Sci., USA, 85, 6987 (1988)).

Said recombinant secretory vector or said recombinant DNA may be introduced into other various mycobacteria such as *Mycobacterium smegmatis,* than BCG, by the electroporation method. Said recombinant secretory vector or said recombinant DNA may be stably held also in the cells of *Mycobacterium smegmatis,* and the cells may express and secrete a fusion protein.

The antigenicity of the fusion protein to be secreted by BCG or *Mycobacterium smegmatis* of the present invention may be conducted by incubating the cells of BCG or *Mycobacterium smegmatis* in Middlebrook 7H9 medium (product of Difco Co.) or in Sauton medium (see J. Bacteriol., 169, 839 (1987)) followed by analyzing the reactivity between the protein collected from the supernatant of the culture and the antibody recognizing the intended foreign antigen by western blotting method (see J. Bacteriol., 170, 3847 (1988)). As the antibody, usable is a rabbit serum (polyclonal antibody) to be obtained by immunizing a rabbit with the intended foreign antigen peptide or an antigen protein containing said peptide along with an adjuvant. Alternatively, also usable is a monoclonal antibody to be obtained by selecting a cell line that produces an antibody reactive with the intended foreign antigen peptide from the hybridoma obtained by fusing the spleen cells of the immunized mouse and myeloma cells by an ordinary method (see Eur. J. Immunol., 6, 511 (1976)), followed by incubating the thus-selected cell line. In the antigen-antibody reaction, if the reactivity between the fusion protein and the antibody is higher than that between the original carrier protein not fused with the intended foreign antigen peptide and the antibody, it is judged that said fusion protein has the antigenicity derived from the intended foreign antigen peptide.

To confirm the antigen-producing capacity of BCG of the present invention using an animal model, the intended foreign antigen peptide or an antigen protein containing said peptide is supported on a suitable solid phase, and the reaction between this and the anti-serum of an animal immunized with BCG is traced by an enzyme-linked immunosorbent assay (ELISA) method or western blotting method.

The effectiveness of the produced antibody against various pathogens may be confirmed by various methods, depending on pathogens. Essentially mentioned are an in vitro growth-inhibiting experiment and an in vivo growth-inhibiting experiment. As one example of the former, known is a method in which said antibody and HIV-1 are added to the culture of human cells which are infectable with HIV-1 and are incubated for a determined period of time and, after the incubation, the virus particles in the culture supernatant are quantitatively determined by an ordinary method, from which the growth-inhibiting effect of said antibody is determined. As one example of the latter, known is a method using an animal model to be prepared by implanting human peripheral lymphocytes which are infectable with HIV-1 into a mouse not having T cells and B cells, such as a serious combined immunodeficiency (SCID) mouse. According to the method, said antibody and HIV-1 are administered to an SCID mouse and the inhibition of the growth of the viruses in the SCID mouse blood is determined.

On the other hand, the CTL inducing capacity may be confirmed by measuring CTL of the intended antigen peptide by a $^{51}$Cr release method using epitope peptide-pulsed cells as the target (see Proc. Natl. Acad. Sci, USA, 85, 3105 (1988)), which is an ordinary method applicable to experiments using mice.

BCG that expresses and secretes the fusion protein may be used as a vaccine. To suspend the BCG cells, used are a physiological saline solution, a phosphate buffer, etc. In general, the vaccine may be administered to human beings and animals by subcutaneous inoculation. As the case may be, however, it may also be administered thereto by peroral administration, intravenous injection, etc. to attain the vaccine effect. The dose of the vaccine is decided to be $2\times10^7$ living cells for subcutaneous inoculation. The vaccine may be applied to three-month-old babies and older than them but cannot be applied to persons infected with tubercle bacillus and tuberculin-positive persons. The side effects after the inoculation of the vaccine are essentially swelling of local lymphonode, local ulcers, etc. but cause few grave disorders.

BCG constituting the present invention secretes the fusion protein to be obtained by inserting a foreign antigen peptide into the molecular surface of the α-antigen derived from mycobacteria. Said fusion protein has noticeably increased antigenicity and immunogenicity to be caused by the foreign antigen peptide. Therefore, when it is inoculated into animals, it is efficiently recognized by B cells that recognize said antigen, thereby effectively inducing the production of an antibody against said antigen. When BCG itself is inoculated into an animal, it continuously secretes said fusion protein, while continuously propagating in the body of the animal. Therefore, it is an extremely effective vaccine.

In most cases, the B cell epitope derived from various pathogens such as HIV-1 exists on the molecular surface at the loop site not having secondary structures such as α-helices and β-sheets. The recombinant secretory vector secreting a fusion protein, which is provided by the present invention, makes BCG secrete and express the B cell epitope derived from such various pathogens while the B cell epitope could be made to maintain its native structure and its high antigenicity. The BCG strain may be a vaccine having high immunogenicity, and the vaccine may induce the production of a high-titer antibody and the significant CTL activity indispensable for protecting human beings and animals from being infected with various viruses, bacteria, parasites, etc.

EXAMPLES

Now, the present invention will be explained more concretely by means of the following examples, in which the following abbreviations are used.

A: adenine
C: cytosine
G: guanine
T: Thymine
DNA: Deoxyribonucleic Acid
Ala: Alanine
Arg: Arginine
Asn: Asparagine
Asp: Aspartic Acid
Gln: Glutamine
Glu: Glutamic Acid
Gly: Glycine
His: Histidine
Ile: Isoleucine
Lys: Lysine
Met: Methionine
Pro: Proline
Ser: Serine
Thr: Threonine
Tyr: Tyrosine
Val: Valine
CTL: Cytotoxic T Cells
ELISA: Enzyme-linked immunosorbent assay
IPTG: Isopropyl-β-D-thiogalactoside
HIV: Human Immunodeficiency Virus
TBS: Tris Buffered Saline
PBS: Phosphate Buffered Saline
SDS-PAGE: Sodium Dodecylsulfate-Polyacrylamide Gel Electrophoresis
MHC: Major Histocompatibility Complex
SCID: Serious Combined Immunodeficiency
TCID50: 50% Tissue Culture Infection Dose

Example 1

Determination of B Cell Epitope of α-Antigen

First, to find out the site surely exposing out of the molecular surface in the hydrophilic region of the α-antigen, the B cell epitope of the α-antigen itself was determined. The hydropathy profile of the α-antigen derived from *Mycobacterium kansasii* (see Infect. Immun., 58, 550 (1990)) was checked to select two most hydrophilic regions in said α-antigen, and to synthesize two DNAs each coding for a peptide composed of about 20 amino acid residues corresponding to each of said regions. One codes for a peptide having a sequence from the 38th Leu residue to the 57th Ala residue in said α-antigen, and the sequence is as follows (SEQ ID NO: 2, SEQ ID NO: 3):

5'-GATCCTCGACGGTCTCCGCGCTCAAGAC-
GACTACAACGGCTGGGACATCAACACCCCGGCC

GAGCTGCCAGAGGCGCGAGTTCTGCT-
GATGTTGCCGACCCTGTAGTTGTGGGGCCGGCTAG-5'

The other codes for a peptide having a sequence from the 184th Ser residue to the 203th Asn residue in said α-antigen, and the sequence is as follows (SEQ ID NO: 4, SEQ ID NO: 5):

5'-GATCAGTGACCCAGCCTGGCAGCGTAAC-
GACCCGTCGCTGCACATTCCGGAGCTGGTCGCCAAC

TCACTGGGTCGGACCGTCGCAT-
TGCTGGGCAGCGACGTGTAAGGAATC-
GACCAGCGGTTGCTAG-5'

A DNA obtained by fusing each of these DNAs to the lowermost stream in the β-galactosidase gene (corresponding to the C-terminal of the intended product) was expressed in the cells of *Escherichia coli* to obtain two fusion proteins. Precisely, each of these DNA fragments was ligated with pUR289 plasmid digested with BamHI (see EMBO J., 3, 1429 (1984)), and the resulting recombinant DNA was introduced into *Escherichia coli* EQ192. Each of the resulting transformants was incubated in L-broth containing 50 μg/ml of ampicillin, at 37° C. for 3 hours by shaking culture, then IPTG was added thereto to have a final concentration of 1 mM, and the incubation was continued for additional two hours at 30° C. The cells were collected by centrifugation. The thus-collected cells were suspended in TBS buffer of 1/10 time by volume the cells, and sonicated at 200 W for 15 minutes to obtain two cell extracts. Each extract contained the intended fusion protein. 10 μl of each of the extracts was subjected to 7.5% SDS-PAGE. The fractionated proteins were blotted onto a nitrocellulose filter. The reactivity of each protein with a rabbit polyclonal antibody to the α-antigen derived from *Mycobacterium kansasii* and that with a rabbit polyclonal antibody to the α-antigen derived from BCG were determined by Western blotting method (see FIG. 1).

The peptide having a sequence from the 38th Leu residue to the 57th Ala residue, that had been fused to β-galactosidase, did not react with both of these antibodies (lanes 2 and 5), while the peptide having a sequence from the 184th Ser residue and the 203th Asn residue, that had been fused to β-galactosidase, had high reactivity with both the antibodies (see lanes 3 and 6). From this, it was known that the B cell epitope common to the above-mentioned two kinds of mycobacteria existed in the region from the 184th Ser residue to the 203th Asn residue. It was presumed that this region is exposed out of the surface of the α-antigen molecule.

Figures 1A, 1B:
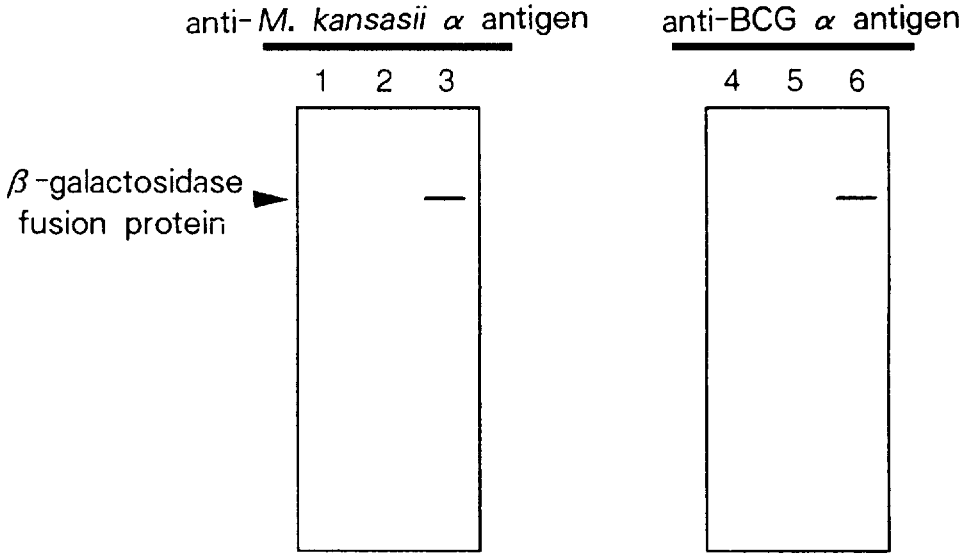
FIG. 1 shows the results of the western blotting method analyses conducted to determine B cell epitope in an α-antigen itself. The left panel (A) (lanes 1, 2 and 3) and the right panel (B) (lanes 4, 5 and 6) show the results obtained by the use of the polyclonal antibody to the α-antigen derived from *Mycobacterium kansasii* and the polyclonal antibody against the α-antigen derived from BCG, respectively.

FIG. 1 is referred to, in which lanes 1 and 4 resulted from the electrophoresis of the cell extracts obtained from *Escherichia coli* EQ192 which carries plasmid pUR298 to express β-galactosidase; lanes 2 and 5 resulted from the electrophoresis of the cell extracts obtained from *Escherichia coli* EQ192 which carries plasmid pUR289+α-Leu38-Ala57 expressing the fusion protein composed of β-galactosidase and the peptide having the sequence from the 38th Leu residue to the 57th Ala residue in the α-antigen; and lanes 3 and 6 resulted from the electrophoresis of the cell extracts obtained from *Escherichia coli* EQ192 which carries plasmid pUR289+α-Ser184-Asn203 expressing the fusion protein composed of β-galactosidase and the peptide having the sequence from the 184th Ser residue to the 203th Asn residue in the α-antigen. The lanes 1, 2 and 3 were labeled with rabbit polyclonal antibodies to the α-antigen derived from *Mycobacterium kansasii,* while the lanes 4, 5 and 6 were labeled with rabbit polyclonal antibodies to the α-antigen derived from BCG. The bands shown in FIG. 1 correspond to the β-galactosidase-fusion proteins.

Example 2

Construction of Fusion Protein Secreting Vector Containing V3 Epitope of HIV-1 Surface Antigen Since it was presumed that the region from the 184th Ser residue to the 203th Asn residue in the α-antigen is exposed out of the molecular surface, an attempt was made to fuse the V3 epitope in the HIV-1 surface antigen and the α-antigen, utilizing the XhoI site corresponding to the position of the 184th Ser residue in the α-antigen gene, in order to make BCG and *Mycobacterium smegmatis* secrete the fusion protein. FIG. 2 is referred to for easily understanding the following description.

In order to obtain a fusion protein to be formed by fusing a peptide composed of 15 amino acid residues of Arg Ile Gln Arg Gly Pro Gly Arg Ala Phe Val Thr Ile Gly Lys (SEQ ID NO: 6) in the V3 epitope of HIV-1 (HTLVIII strain) to the position of the above-mentioned 184th Ser residue (the position of XhoI site in the DNA), a DNA fragment to be formed by completely digesting plasmid pKAH200 containing the α-antigen gene with XhoI was separated to be a vector DNA. On the other hand, a gene coding for the peptide comprising said 15 amino acid residues was chemically synthesized. Its sequence is as follows (SEQ ID NO: 7, SEQ ID NO: 8):

5 '-TCGAGTCGGATCCAGAGGGGCCCTGG-
TAGGGCGTTCGTCACCATCGGCAAG

CAGCCTAGGTCTCCCCGGGACCATCCCG-
CAAGCAGTGGTAGCCGTTCAGCT-5' (XhoI site)

Said synthetic DNA was ligated with the above-mentioned vector DNA, and the resulting recombinant DNA was introduced into *Escherichia coli* HB101, by which the recombinant DNA was amplified in the resulting transformant. Next, in order to isolate the fusion protein gene as a KpnI fragment, KpnI linker was inserted into the HindIII site derived from pUC vector. The thus-obtained plasmid was digested with KpnI to isolate KpnI—KpnI DNA fragment containing the fusion protein gene. The KpnI—KpnI DNA fragment was cloned into the KpnI site in mycobacteria/*Escherichia coli* shuttle vector pIS18 (see Infect. Immun., 58, 4049 (1990)) to obtain a recombinant secretory vector which was named pIJK-V3 (HTLVIIIB-XhoI).

A necessary recombinant secretory vector was prepared in order to make BCG and *Mycobacterium smegmatis* secrete the control fusion protein to be obtained by fusing the V3 epitope of HIV-1 (HTLVIIIB strain) and the α-antigen. In this example, a fusion protein obtained by fusing a peptide composed of 15 amino acid residues of Arg Ile Gln Arg Gly Pro Gly Arg Ala Phe Val Thr Ile Gly Lys (SEQ ID NO: 6) in the V3 epitope of HIV-1 (HTLVIIIB strain) to the position of the PstI site corresponding to the position of the 279th Gln residue in the vicinity of the C-terminal of the α-antigen was used as the control. A DNA fragment to be formed by completely digesting plasmid pKAH200 containing the α-antigen gene with PstI was isolated to be a vector DNA. On the other hand, the gene coding for the 15 amino acids were chemically synthesized. Its sequence is as follows (SEQ ID NO: 9, SEQ ID NO: 10):

5'-GCGGATCCAGAGGGGCCCTGG-
TAGGGCGTTCGTCACCATCGGCAAGTAGCTGCA-3'

3'-ACGTCGCCTAGGTCTCCCCGGGACCATC-
CCGCAAGCAGTGGTAGCCGTTCATCG-5' (PstI site)

Said synthetic DNA was ligated with the above-mentioned vector DNA, then the thus-obtained recombinant DNA was introduced into *Escherichia coli* HB101, and the recombinant DNA was amplified in the transformant. Next, in order to isolate the fusion protein gene as a KpnI fragment, KpnI linker was inserted into the pUC vector-derived HindIII site. The thus-obtained plasmid was digested with KpnI to isolate a KpnI—KpnI DNA fragment containing the fusion protein gene. The KpnI—KpnI DNA fragment was cloned into the KpnI site in mycobacteria/*Escherichia coli* shuttle vector pIS18 (see Infect. Immun., 58, 4049 (1990)) to obtain a recombinant secretory vector which was named pIJK-V3(HTLVIIIB-PstI).

Example 3

Expression and Secretion of HIV-1 V3 Epitope-α-Antigen Fusion Protein by *Mycobacterium smegmatis*

The recombinant secretory vectors pIJK-V3(HTLVIIIB-XhoI) and pIJK-V3(HTLVIIIB-PstI) that had been constructed in Example 2 were separately introduced into *Mycobacterium smegmatis* ATCC607 by a known method (see Proc. Natl. Acad. Sci., USA, 85, 6987 (1988)). The thus-obtained two transformants were separately incubated in 70 ml of a Sauton medium containing 30 μg/ml of kanamycin (see J. Bacteriol., 169, 839 (1987)), at 37° C. for 2 weeks by static culture. After the incubation, the cultures each were subjected to centrifugation and filtration through a millipore filter to remove the cells therefrom. Thus, a supernatant was obtained from each culture. To 0.5 ml of each supernatant, added was the same amount of an aqueous 10% trichloroacetic acid solution, and this was further incubated for 30 minutes at 0° C. This was then centrifuged to precipitate the proteins. Each of the resulting precipitates was suspended in 20 μl of a sample buffer for SDS-PAGE (comprising 60 mM tris, 2% SDS, 5% 2-mercaptoethanol, 10% glycerin, 0.1% bromophenol blue) and dissolved therein by heating at 95° C. for 5 minutes to obtain a sample for electrophoresis. Each of the thus-prepared samples was fractionated by 15% SDS-PAGE. After the electrophoresis, the proteins were blotted onto a nitrocellulose membrane filter by an ordinary method and analyzed by Western blotting method. The results are shown in FIG. 3.

The fusion protein (lane 2) formed by fusing the peptide composed of the 15 amino acid residues derived from HTLVIIIB strain to the position of the 184th Ser residue of the α-antigen showed the reactivity with the neutralizing monoclonal antibody gp120N to the V3 epitope of HIV-1 by 50 to 100 times higher than the fusion protein (lane 3) formed by fusing the peptide composed of the 15 amino acid residues derived from HTLVIIIB strain to the position of the 279th Gln residue of the α-antigen. The results show that when the V3 epitope was expressed in such a way that it was exposed out of the molecular surface of the α-antigen, the antigenicity of the V3 epitope was greatly improved.

FIG. 3 is referred to, in which the lane 1 shows the supernatant from the culture of *Mycobacterium smegmatis* which carried vector pIJK-1 to secrete only the α-antigen (see Infect. Immun., 58, 4049 (1990)); the lane 2 shows the supernatant from the culture of *Mycobacterium smegmatis* which carried pIJK-V3(HTLVIIIB-XhoI), and this is to check the antigen-antibody reaction of the fusion protein formed by fusing the peptide composed of the HTLVIIIB-derived 15 amino acid residues to the position of the 184th Ser residue in the α-antigen; the lane 3 shows the supernatant from the culture of *Mycobacterium smegmatis* which carried pIJK-V3(HTLVIIIB-PstI), and this is to check the antigen-antibody reaction of the fusion protein formed by fusing the peptide composed of the HTLVIIIB-derived 15 amino acid residues to the position of the 279th Gln residue in the α-antigen.

For the labeling, used was a neutralizing monoclonal antibody gp120N to the V3 epitope of HIV-1. This antibody is available from DuPont Co., USA.

Example 4

Construction of Fusion Protein Secreting Vector Containing V3 Epitope of HIV-1(Japan) Surface Antigen Examples 2 and 3 demonstrated the experiments relating to the fusion protein obtained by fusing the peptide composed of the 15 amino acid residues of Arg Ile Gln Arg Gly Pro Gly Arg Ala Phe Val Thr Ile Gly Lys (SEQ ID NO: 6) in the HIV-1(HTLVIIIB) V3 epitope to the position of the 184th Ser residue in the α-antigen. This example is to demonstrate an experiment relating to a fusion protein to be obtained by fusing a peptide composed of 19 amino acid residues of Asn Thr Arg Lys Ser Ile His Ile Gly Pro Gly Arg Ala Phe Tyr Ala Thr Gly Ser (SEQ ID NO: 1) in HIV-1 (Japan) V3 epitope to the position of the 184th Ser residue in the α-antigen.

FIG. 2 is referred to for easily understanding the following description.

In order to obtain a fusion protein to be formed by fusing a peptide composed of 19 amino acid residues of Asn Thr Arg Lys Ser Ile His Ile Gly Pro Gly Arg Ala Phe Tyr Ala Thr Gly Ser (SEQ ID NO: 1) in HIV-1(Japan) V3 epitope to the position of the 184th Ser residue in the α-antigen (the position of XhoI site in the DNA), a DNA fragment to be formed by completely digesting plasmid pKAH200 containing the α-antigen gene with XhoI was separated to be a vector DNA. On the other hand, a gene coding for the peptide comprising said 19 amino acid residues was chemically synthesized. Its sequence is as follows (SEQ ID NO: 11, SEQ ID NO: 12):

5'-TCGAGTAACACGAGGAAGAGCATCCA-
CATCGGGCCCGGGAGGGCATTCTACGCCACCGGG

CATTGTGCTCCTTCTCGTAGGTGTAGC-
CCGGGCCCTCCCGTAAGATGCGGTGGCCCAGCT-5'

Said synthetic DNA was ligated with the above-mentioned vector DNA, and the resulting recombinant DNA was introduced into Escherichia coli HB101, by which the recombinant DNA was amplified in the resulting transformant. Next, in order to isolate the fusion protein gene as a KpnI fragment, KpnI linker was inserted into the HindIII site derived from pUC vector. The thus-obtained plasmid was digested with KpnI to isolate a KpnI—KpnI DNA fragment containing the fusion protein gene. The KpnI—KpnI DNA fragment was cloned into the KpnI site in mycobacteria/*Escherichia coli* shuttle vector pIS18 (see Infect. Immun., 58, 4049 (1990)) to obtain a recombinant secretory vector which was named pIJK-V3(Japan-XhoI).

Example 5

Expression and Secretion of HIV-1 V3 Epitope-α-Antigen Fusion Protein by *Mycobacterium smegmatis* and BCG The recombinant secretory vector pIJK-V3(Japan-XhoI) that had been constructed in Example 4 was introduced into *Mycobacterium smegmatis* ATCC607 by a known method (see Proc. Natl. Acad. Sci., USA, 85, 6987 (1988)). The thus-obtained transformant was incubated in 70 ml of a Sauton medium containing 30 μg/ml of kanamycin (see J. Bacteriol., 169, 839 (1987)), at 37° C. for 2 weeks by static culture. After the incubation, the culture was subjected to centrifugation and filtration through a millipore filter to remove the cells therefrom. Thus, a supernatant was obtained from the culture. To 0.5 ml of the supernatant, added was the same amount of an aqueous 10% trichloroacetic acid solution, and this was further incubated for 30 minutes at 0° C. This was then centrifuged to precipitate the proteins. The resulting precipitate was suspended in 20 μl of a sample buffer for SDS-PAGE (comprising 60 mM tris, 2% SDS, 5% 2-mercaptoethanol, 10% glycerin, 0.1% bromophenol blue) and dissolved therein by heating at 95° C. for 5 minutes to obtain a sample for electrophoresis. Thus-prepared sample was fractionated by 15% SDS-PAGE electrophoresis. After the electrophoresis, the proteins were blotted onto a nitrocellulose membrane filter by an ordinary method and analyzed by Western blotting method. The results are shown in FIG. 3. The results show that the fusion protein formed by fusing the peptide composed of the HIV-1(Japan)-derived 19 amino acid residues to the position of the 184th Ser residue in the α-antigen also strongly reacts with the neutralizing monoclonal antibody μ 5.5 to the HIV-1 V3 epitope (see lane 5). From the fact, it is understood that, when the V3 epitope of HIV-1(Japan) was expressed in such a way that it was exposed out of the molecular surface of the α-antigen, the antigenicity of the V3 epitope was also greatly improved.

FIG. 3 is referred to, in which the lane 4 shows the control supernatant from the culture of *Mycobacterium smegmatis* which carried pIJK-1; and the lane 5 shows the supernatant from the culture of *Mycobacterium smegmatis* which carried pIJK-V3(Japan-XhoI), and this is to check the antigen-antibody reaction of the fusion protein formed by fusing the peptide composed of the HIV-1(Japan)-derived 19 amino acid residues to the position of the 184th Ser residue in the α-antigen.

For the labeling, used was a neutralizing monoclonal antibody μ 5.5 to the V3 epitope of HIV-1. This antibody was obtained by immunizing a mouse with a trimeric peptide formed by adding Cys residues to both the terminals of the above-mentioned peptide composed of the above-mentioned 19 amino acid residues (SEQ ID NO: 1), then fusing the spleen cells isolated from the thus-immunized mouse and mouse myeloma cells to obtain hybridoma cells, and incubating the hybridoma cells.

Considering the object for developing a vaccine against the HIV-1 strain which is the most popular one among Japanese HIV-1 carriers-derived viruses, BCG was made to secrete the fusion protein formed by fusing the peptide composed of the 19 amino acid residues derived from HIV-1(Japan) to the position of the 184th Ser residue in the α-antigen. To carry out the experiment, the same process as that employed in carrying out the above-mentioned experiment using *Mycobacterium smegmatis* was employed. The results obtained by analyzing the secreted, fusion protein by the same Western blotting method are shown in FIG. 3. The results show that, even when the fusion protein formed by fusing the peptide composed of the HIV-1(Japan)-derived 19 amino acid residues to the position of the 184th Ser residue in the α-antigen was secreted by BCG, it strongly reacted with the neutralizing monoclonal antibody μ 5.5 to the HIV-1 V3 epitope (see lane 7). The thus-obtained BCG strain was named BCG-V3 and was used in the following tests using animal models. *Mycobacterium bovis* BCG-V3 has been deposited with National Institute of Bioscience and Human Technology, Agency of Industrial Science and Technology, Ministry of International Trade and Industry, Japan under the accesession number of FERM BP-4759.

FIG. 3 is again referred to, in which the lane 6 shows the control supernatant from the culture of *Mycobacterium bovis* BCG which carried pIJK-1; and the lane 7 shows the supernatant from the culture of *Mycobacterium bovis* BCG which carried pIJK-V3(Japan-XhoI), and this is to check the antigen-antibody reaction of the fusion protein formed by fusing the peptide composed of the HIV-1(Japan)-derived 19 amino acid residues to the position of the 184th Ser residue in the α-antigen.

For the labeling, used was the neutralizing monoclonal antibody $\mu$ 5.5 to the HIV-1 V3 epitope.

Example 6

Production of Antibody to HIV-1 V3 Site in Guinea Pigs

BCG-V3 and BCG-α that expresses only the α-antigen derived from *Mycobacterium kansasii* each were incubated in 5 ml of a Middlebrook 7H9 medium (product of Difco Co.) at 37° C. by shaking culture, and the cells were collected at the point when OD610 nm became about 0.6 (logarithmic growth phase). These were washed once with PBS and then suspended in 10 ml of PBS. One ml of the suspension containing the BCG-V3 cells (5 mg, containing about $10^8$ BCG cells) was subcutaneously inoculated into four guinea pigs, while the same amount of the suspension containing BCG-α cells was subcutaneously inoculated into other three guinea pigs. After 6 weeks, the blood was collected from each animal, and its anti-V3 antibody titer was measured by ELISA using a V3 peptide antigen (composed of 19 amino acids) (see Table 1). The blood from the negative control of each of all the BCG-α-immunized guinea pig showed the antibody titer of below the detectable limit. However, in all the four BCG-V3-immunized guinea pigs, high-titer antibody production was induced, yielding the anti-V3 antibody titer of above 120 to 640 times. Among them, the antibody titers induced in the two animals were a sufficient level enough to protect chimpanzees from being infected with HIV-1 (see Nature, 345, 622 (1990)).

Table 1 shows the test results indicating the production of the anti-V3 antibody in guinea pigs, in which "Normal", "BCG-V3-1 to BCG-V3-4" and "BCG-α-K-1 to BCG-α-K-3" mean "non-immunized guinea pig", "four guinea pigs immunized with BCG-V3" and "three guinea pigs immunized with BCG-α", respectively.

TABLE 1

Serum Anti-V3 Antibody Titer by HIV V3-Peptide ELISA

| Guinea pigs | Anti-V3-Antibody Titer |
|---|---|
| Normal | 0 |
| BCG-V3-1 | 640 |
| BCG-V3-2 | 160 |
| BCG-V3-3 | 120 |
| BCG-V3-4 | 320 |
| BCG-α-K-1 | 0 |
| BCG-α-K-2 | 0 |
| BCG-α-K-3 | 0 |

After 6 weeks of subcutaneous inoculation of 5 mg of the recombinant BCG, anti-V3-antibody titer was measured by ELISA.

Example 7

Measurement of in vitro Virus Neutralizing Activity of Sera of Guinea Pigs immunized with BCG-V3

In vitro virus neutralizing activity was assayed using sera of four BCG-V3 immunized guinea pigs obtained after 6 weeks in Example 6. Human peripheral blood lymphocytes (PBL) were stimulated with phytohemagglutinin for one day and used as target cells. Immunoglobulin G (IgG) fraction of guinea pigs serum and $2000TCID_{50}$ of HIV-1 MN strain were preincubated at 37° C. for one hour and mixed with the target cell culture. About one week later, when a cytopathic effect was obsereved on the target cells, HIV particles in the cell culture supernatant were assayed using an ELISA kit for the detection of p24 core protein. The results are shown in Table 2. Remarkable HIV-1 neutralizing activity was observed in the sera of all the four guinea pigs immunized with BCG-V3 but not in the serum of the normal guinea pig. This demonstrates that the anti-V3 antibody obtained in Example 6 has in fact the activity inhibiting HIV-1 propagation.

In Table 2, p24 protein concentration in the culture supernatant of the target cells were expressed by pg/ml unit at each guinea pig serum IgG concentration used for the reaction with the viruses. It can be said that a serum has an HIV neutralizing activity if p24 protein concentration obsereved is lower than that observed when the normal guinea pig serum is used.

TABLE 2

Virus Neutralizing Activity of Sera of Guinea Pigs Immunized with BCG-V3

| Ig concentration ($\mu$g/ml) | BCG-V3-1 | BCG-V3-2 | BCG-V3-3 | BCG-V3-4 | Normal | $\mu$ 5.5 |
|---|---|---|---|---|---|---|
| 0 | 2390 | 2390 | 2390 | 2390 | 2390 | 2390 |
| 1 | 1308 | 1656 | 2880 | 1906 | 2250 | 2096 |
| 10 | 1184 | 635 | 1427 | 804 | 1815 | 1 |
| 50 | 961 | 19 | 906 | 47 | 1921 | 1 |

"Normal" indicates the serum of the normal guinea pig, "BCG-V3-1 to BCG-V3-4" sera of the four guinea pigs immunized with BCG-V3, and "$\mu$ 5.5" a neutralizing monoclonal antibody. The amounts of virus core protein p24 in the culture supernatant of the target cells are expressed by pg/ml unit.

Example 8

Measurement of in vivo Virus Neutralizing Activity of Sera of Guinea Pigs immunized with BCG-V3 using SCID Beige Mice SCID beige mice (lacking natural killer cells in addition to T cells and B cells) were injected with $2\times10^7$ cells of human peripheral blood lymphocytes intraperitoneally. After two weeks, about $6000TCID_{50}$ of HIV-1 MN strain and 10 mg of immunoglobulin fraction of guinea pigs inoculated with BCG-V3 obtained in Example 6 were injected intravenously at the same time. After 84 hours, the blood was removed and the target cells were collected. The target cells were cultured with human peripheral blood lymphocytes stimulated with phytohemagglutinin for seven days. Then, the virus concentration in the culture supernatant was measured in the similar manner to that in Example 7. The results are shown in Table 3. In each target cells, about 100 pg/ml of p24 was detected when the normal guinea pig serum was used, while p24 was not detected when the BCG-V3-2 serum was used. This demonstrates that the anti-V3 antibody in the BCG-V3-2 serum has HIV-1 neutralizing activity in vivo and can protect HIV-1 infection to peripheral blood lymphocytes in SCID mice.

Table 3 shows the p24 protein concentration (pg/ml) in the culture supernatant of peripheral blood mononuclear cells, peritoneal exudate cells, and spleen cells of the SCID beige mice immunized with HIV-1 MN strain and guinea pig serum immunoglobulin. "<30" means undetectable level in the assay system.

TABLE 3

In vivo Virus Neutralizinq Activity using SCID beige mice

| Target cells | Normal guinea pig IgG | BCG-V3-2 guinea pig IgG |
|---|---|---|
| Peripheral blood mononuclear cells | 95 | <30 |
| Peritoneal exudate cells | 90 | <30 |
| Spleen cells | 104 | <30 |

SCID beige mice were injceted with $2 \times 10^7$ cells of human peripheral blood lymphocytes intraperitoneally. After two weeks, HIV-1 MN strain and 10 mg of guinea pig serum IgG were injected intravenously. After 84 hours, the cells were collected and cultured for seven days. The virus core protein p24 concentration in the culture supernatant observed are shown in pg/ml unit.

Example 9

Induction of CTL in Mice

Five Balb/c mice each were subcutaneously inoculated with 0.1 mg of BCG-V3. After 2 weeks, the spleen cells were isolated from each mouse and were re-stimulated with 10 $\mu$g/ml of the V3 peptide (composed of 19 amino acids) for 7 days to prepare effector cells. Using P815 cells (MHC class I: H2d) that had been pulsed with the V3 peptide, as the target cells, the CTL activity of the effector cells was determined by a Cr release method. Significant induction of the CTL activity was confirmed in all the cells derived from the five mice (see FIG. 4A). On the other hand, when SW5147 cells having MHC class I H2k molecules were used as the target cells, the effector cells did not show this activity. From these facts, it is considered that this activity results from the MHC class I-restricted CTL (see FIG. 4B).

Example 10

Measurement of Clinically Isolated Virus Neutralizing Activity of Sera of Guinea Pigs immunized with BCG-V3

It has been reported that a neutralizing antibody derived from subunit gp120 vaccine (produced by gene recombinant animal cells) to which attention was paid as a candidate vaccine for preventing AIDS infection, can neutralize laboratory strains such as MN strain but cannot clinically isolated strains (see AIDS Res. Human Retroviruses, 10, 631–632 (1994)). We measured clinically isolated HIV-1 strain neutralizing activity of sera obtained six weeks after subcutaneous inoculation of 5 mg of BCG-V3 to two groups of guinea pigs each having 20 animals, using the in vitro neutralization assay as described in Example 7. Clinically isolated viruses used in this assay, HIV-A and HIV-B, were obtained by stimulating peripheral blood mononuclear cells of Japanese HIV carriers with phytohemagglutinin and incubating the cells with normal human peripheral blood mononuclear cells in RPM1640 medium (product of Gibco). Cell-free viruses in the culture supernatant were extracted and reverse-transcribed using OD3 primer (nt 7345–7369= 5'-AAATTCCCCTCCACAATTAAAACTG-3' (SEQ ID NO: 19) and a reverse transcriptase to prepare a DNA. Using the DNA as a template, PCR reaction was conducted using two kinds of primers EB2 (nt 6989–7009 to which a sequence recognized by BamHI had been added=5'-GCCGGATCCTCAACTCAACTGCTGTTAAAT-3' (SEQ ID NO: 20)) and EC2 ((nt 7314–7336 to which a sequence recognized by PstI and the stop codon had been added=5'-GCTCTGCAGTCAAATTTCTGGGTCCCCTCCTGAGG-3' (SEQ ID NO: 21)) which sandwich the V3 region to ampify the DNA. The amplified DNA was digested with BamHI and PstI to prepare a fragment which was then cloned into pUC18 vector. A nucleotide sequence of the thus cloned DNA was determined by a 373A DNA sequencer (available from Applied Biosystems-Perkin Elmer Co.) to presume an amino acid sequence of the V3 region. The clinically isolated virus (100 TCID50) was mixed with immunoglobulin fraction obtained by purifying mixed sera from the immunized 20 guinea pigs on protein A sepharose column (Pharmacia P-L Biochemicals) and incubated at 37° C. for 60 minutes. The mixture was mixed with $10^6$ cells of normal human peripheral blood mononuclear cells stimulated with phytohemagglutinin and incubated with shaking at 37° C. for 60 minutes. The cells were washed with PBS and cultured in RPM1640 medium containing recombinant human IL-2 (40 units/ml) for 7 days. HIV concentration in the supernatant was determined by p24 antigen ELISA kit (available from Dinabot, Tokyo). The results are shown in FIG. 5B wherein neutralizing activity is expressed by the inhibition ratio of p24 concentration obtained when the antibody was added to the system as compared to that obtained when the antibody was not added.

The experiments were conducted for the guinea pigs sera of the two groups, GP-1 and GP-2, with respect to two kinds of viruses A and B. The serum immunoglobulin of BCG-α immunized guinea pigs or unimmunized guinea pigs showed almost no neutralizing activity, while that of BCG-V3 immunized guinea pigs showed such very high neutralizing activity that 90% inhibition concentration was about one $\mu$g/ml. The amino acid sequence of the neutralizing epitope (the shadowed area in FIG. 5A) in the V3 region of the two kinds of viruses were identical with the consensus sequence of HIV MN strain and the Japanese strain which were introduced into BCG-V3. This demonstrates that the antibody can neutralize any viruses which have identical amino acid sequence with the V3 neutralizing epitope, regardless of strains isolated from HIV carriers or strains subcultured in laboratory like MN strain.

Example 11

Cross Reactivity of Anti-V3 antibody produced in Guinea Pigs

The mixed sera of the group of 20 guinea pigs prepared in Example 10 (6 weeks after BCG-V3 immnunization) were assayed for cross reactivity with V3 regions of Thai A and Thai B viruses. It is generally recognized that North America (MN strain) and Japanese strains which belong to cladeB do not serologically cross react with Thai strains which belong to cladeE. Cross reactivity was examined by ELISA method using as an antigen, Thai A V3 peptide composed of 19 amino acids (Asn Thr Arg Thr Ser Ile Thr Ile Gly Pro Gly Gln Val Phe Tyr Arg Thr Gly Asp)(SEQ ID NO: 18) and Thai B V3 peptide composed of 19 amino acids (Asn Thr Arg Lys Ser Ile His Leu Gly Pro Gly Gln Ala Trp Tyr Thr Thr Gly Gln)(SEQ ID NO: 22) which were conjugated with keyhole limpet hemocyanin (KLH), a carrier protein. The results are shown in FIG. 6.

Normal guinea pig serum (control) hardly cross reacts with Thai A V3 peptide or Thai B V3 peptide, while BCG-V3 immunized guinea pig sera cross react with both Thai A V3 peptide and Thai B V3 peptide. This suggests the possibility that BCG-V3 immunized guinea pig sera neutralize Thai viruses in addition to North America and Japanese viruses.

Example 12

Production of Neutralizing Antibody in Simian

Four male cynomolgus monkeys (7 to 8 year old, #2796 to #2799) were subcutaneously inoculated with 30 mg of BCG-V3 ($6\times10^8$ cells) for (#2796 and #2797) and 5 mg of BCG-V3 ($1\times10^8$ cells) for (#2798 and #2799). Anti-V3 antibody titer in the sera after 2, 4, 6, 8, 12 and 27 weeks was assayed by ELISA method using the V3 peptide (19 amino acids) antigen conjugated with KLH. Antibody production was induced in all the four animals. Change in the level of anitbody titer for two animals (#2797 and #2799) is shown in FIG. 7. Antibody production of a titer of higher than $10^6$ was observed. However, the titer tended to gradually decrease 10 weeks after immunization. HIV-1 MN strain neutralizing activity of the sera after 4 weeks was examined by in vitro assay as described in Example 10. The results are shown in FIG. 8. The serum antibodies of all the animals have neutralizing activity. In particular, the sera of the monkeys inoculated with 5 mg of BCG-V3 (#2798 and #2799) were found to have such strong neutralizing activity that 90% inhibition concentration is about 10 $\mu$g/ml.

Example 13

Protection against HIV-SIV Chimera Virus (SHIV) in Monkeys

It has been reported that HIV-SIV chimera virus (SHIV) which is a simian immnunodeficiency virus (SIV) infectable with cynomolgus monkeys and whose envelope (gp120, gp41 portion) has been replaced by that of HIV-1 is also infectable with cynomolgus monkeys. The V3 region of a molecular clone of NM-3rN obtained by converting the envelope portion into that derived from HIV-1(HTLVIIIB strain) (see J. Virol. 65, 3514 (1991)) was replaced by the sequence derived from HIV-1 Japanese strain to prepare a chimera virus NM-3rNJ1. A method for the construction of the chimera virus is shown in FIG. 9. The NM-3rN gene was digested with EcoRI and HpaI to obtain the envelope region, which was then subcloned to EcoRI-HpaI site of pUC18 to which an HpaI linker (available from Takara Shuzo) had been inserted to HincII site. The plasmid thus obtained was digested with BglII to separate a larger fragment which was used as a vector.

On the other hand, as described in Example 10, a virus RNA was isolated from blood of the Japanese HIV carrier A, reverse transcribed into DNA which was amplified by PCR method. The DNA was subcloned as BamHI-PstI fragment into pUC18. The plasmid was digested with BglII to obtain a DNA fragment containing the V3 region. The fragment was then ligated with the above-mentioned vector to obtain a recombinant plasmid. The plasmid was introduced into *Escherichia coli* HB101 and amplified in the transformant. A small fragment obtained by digesting the plasmid with EcoRI and HpaI was ligated with a large fragment obtained by digesting NM-3rN with EcoRI and HpaI to obtain NM-3rNJ1 having the HIV-1 V3 region gene derived from the Japanese strain. The plasmid NM-3rNJ1 was transfected into M8166 cells by conventional calcium phosphate method. The cells were incubated in RPM1640 meidum for one week. The virus (SHIV) released into the culture supernatant was again transfected into M8166 cells whcih were then incubated for one week. The thus obtained virus in the culture supernatant was used for infection experiment.

38 Weeks after the immnunization, the two simians (#2797 and #2799) each were subjected to booster by subcutaneous inoculation with 100 $\mu$g of a fusion protein of an $\alpha$-antigen and a maltose binding protein expressed in *Escherichia coli* and purified on amylose resin column to which the V3 peptide of 19 amino acids had been inserted. Two weeks after the booster, the increase in anti-V3 antibody titer was confirmed and then SHIV(MN) $10TCID_{50}$ was intravenously injected. After 2, 4 and 6 weeks of the challenge, blood was collected. The peripheral blood mononuclear cells were isolated and two times dilution series from the cells ($5\times10^6$ cells) each were incubated with M8166 cells. After one week incubation, chimera virus concentration in the culture supernatant was assayed by an ELISA kit for assaying an SIV p27 antigen (available from Ortho). The results obtained after 4 weeks are shown in FIG. 10. In #2797, chimera virus infection was observed when cell concentration was $2.5\times10^6$ or more. However, The virus amount produced was significantly lower than negative control wherein normal cynomolgus monkey was inoculated with the chimera virus $10TCID_{50}$. In #2799, chimera virus was not detected at all. This demonstrates that the animal was perfectly protected from SHIV infection.

Example 14

Establishment of BCG Strain Expressing HIV-1 gp41 Neutralizing Epitope

A recombinant BCG was prepared which expresses and secretes an $\alpha$-antigen fusion protein with gp41 neutralizing epitope which has been reported to be recognized by an antibody having strong virus neutralizing activity among B cell epitopes other than HIV-1 V3 epitope (see J. Virol. 67, 6642–6647 (1993)). By the similar manner described in Examples 2 and 3, genes each coding for 6 amino acids (Glu Leu Asp Lys Trp Ala (SEQ ID NO: 23)) of the gp41 epitope instead of the V3 epitope and 13 amino acids (to the N-terminal end of the gp41 epitope, amino acids had been added)(Lys Asn Glu Gln Glu Leu Leu Glu Leu Asp Lys Trp Ala (SEQ ID NO: 13) (each having a cohesive end which makes the gene to be inserted into XhoI recognition site) were chemically synthesized and used for cloning. The DNA sequences are as follows:

5'-TCGAGTGAGCTGGACAAGTGGGCT

CACTCGACCTGTTCACCCGAAGCT-5'

(SEQ ID NO: 24, SEQ ID NO: 25)(coding for 6 amino acids), and

5'-TCGAGTAAGAACGAGCAGGAGCTGCTG-
GAGCTGGACAAGTGGGCT

CATTCTTGCTCGTCCTCGACGACCTC-
GACCTGTTCACCCGAAGCT-5'

(SEQ ID NO: 26, SEQ ID NO: 27)(coding for 13 amino acids).

In the same manner as the case of the V3 epitope as shown in FIG. 2, the DNA fragments were ligated with a vector DNA obtained by completely digesting the plasmid pKAH200 with XhoI to prepare a recombinant DNA which was then transformed into *Escherichia coli* HB101 and amplified in the transformant. In order to isolate a gene coding for a fusion protein as a KpnI fragment, a KpnI linker was inserted into HindIII site derived from pUC vector and the thus obtained plasmid was digested with KpnI to isolate a KpnI—KpnI DNA fragment. The DNA fragment was cloned into KpnI site of pIS18 vector to obtain a recombinant secretory vector. The thus obtained vectors were named pIJKgp41-X6 for 6 amino acids and pIJKgp41-X13 for 13 amino acids.

The vectors each were introduced into BCG Tokyo strain by known method (see Proc. Natl. Acad. Sci. USA 85, 6987

(1988)). The thus obtained transformants each were cultured with shaking in 5 ml of Middlebrook 7H9 (product of Difco) containing 30 μg/ml of kanamycin at 37° C. for 6 weeks. After the supernatant was filtered through milipore filter to remove bacteria, equal volume of SDS-PAGE sample buffer of two times concentration was added. The mixture was heated at 95° C. for 5 minutes and then subjected to 15% SDS-PAGE. After fractionation, the mixture was blotted on a nitrocellulose filter in conventional manner and assayed by western blotting method. The results are shown in FIG. 11.

Both of BCG carrying pIJKgp41-X6 (lane 2) and BCG carrying pIJKgp41-X13 (lane 3) showed remarkable reactivity with neutralizing monoclonal antibody 2F5 which recognizes gp41 epitope (Waldheim Pharmazeutika, Austria), with the latter showing slightly stronger reactivity. The above demonstrates that similarly, other neutralizing epitopes than the V3 epitope can be inserted into the molecular surface of an α-antigen to be expressed and secreted. These BCG strains are named BCG-gp41-X6 (6 amino acids) and BCG-gp41-X13 (13 amino acids).

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: HUMAN IMMUNODEFICIENCY VIRUS
( B ) STRAIN: HIV-1

( x i ) SEQUENCE DESCRIPTION: SEQ ID NO:1:

Asn Thr Arg Lys Ser Ile His Ile Gly Pro Gly Arg Ala Phe Tyr Ala
1 5 10 15

Thr Gly Ser ( 2 ) INFORMATION FOR SEQ ID NO:2:

( i ) SEQUENCE CHARACTERISTICS:
( A ) LENGTH: 61 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:2:

GATCCTCGAC GGTCTCCGCG CTCAAGACGA CTACAACGGC TGGGACATCA ACACCCCGGC 60

C 61

( 2 ) INFORMATION FOR SEQ ID NO:3:

( i ) SEQUENCE CHARACTERISTICS:
( A ) LENGTH: 61 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:3:

GATCGGCCGG GGTGTTGATG TCCCAGCCGT TGTAGTCGTC TTGAGCGCGG AGACCGTCGA 60

G 61

( 2 ) INFORMATION FOR SEQ ID NO:4:

-continued ( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:4:

GATCAGTGAC CCAGCCTGGC AGCGTAACGA CCCGTCGCTG CACATTCCGG AGCTGGTCGC 60

( 2 ) INFORMATION FOR SEQ ID NO:5:

( i ) SEQUENCE CHARACTERISTICS:
( A ) LENGTH: 64 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:5:

GATCGTTGGC GACCAGCTAA GGAATGTGCA GCGACGGGTC GTTACGCTGC CAGGCTGGGT 60

CACT 64

( 2 ) INFORMATION FOR SEQ ID NO:6:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: HUMAN IMMUNODEFICIENCY VIRUS
( B ) STRAIN: HIV-1 (JAPAN)

( x i ) SEQUENCE DESCRIPTION: SEQ ID NO:6:

Arg Ile Gln Arg Gly Pro Gly Arg Ala Phe Val Thr Ile Gly Lys
1 5 10 15

( 2 ) INFORMATION FOR SEQ ID NO:7:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:7:

TCGAGTCGGA TCCAGAGGGG CCCTGGTAGG GCGTTCGTCA CCATCGGCAA G 51

( 2 ) INFORMATION FOR SEQ ID NO:8:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

-continued ( x i ) SEQUENCE DESCRIPTION: SEQ ID NO:8:

TCGACTTGCC GATGGTGACG AACGCCCTAC CAGGGCCCCT CTGGATCCGA C 51

( 2 ) INFORMATION FOR SEQ ID NO:9:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:9:

GCGGATCCAG AGGGGCCCTG GTAGGGCGTT CGTCACCATC GGCAAGTAGC TGCA 54

( 2 ) INFORMATION FOR SEQ ID NO:10:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:10:

GCTACTTGCC GATGGTGACG AACGCCCTAC CAGGGCCCCT CTGGATCCGC TGCA 54

( 2 ) INFORMATION FOR SEQ ID NO:11:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:11:

TCGAGTAACA CGAGGAAGAG CATCCACATC GGGCCCGGGA GGGCATTCTA CGCCACCGGG 60

( 2 ) INFORMATION FOR SEQ ID NO:12:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:12:

TCGACCCGGT GGCGTAGAAT GCCCTCCCGG GCCCGATGTG GATGCTCTTC CTCGTGTTAC 60

( 2 ) INFORMATION FOR SEQ ID NO:13:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:

-continued (A) ORGANISM: HUMAN IMMUNODEFICIENY VIRUS
(B) STRAIN: HIV-1

(xi) SEQUENCE DESCRIPTION: SEQ ID NO:13:

Lys Asn Glu Gln Glu Leu Leu Glu Leu Asp Lys Trp Ala
1 5 10

(2) INFORMATION FOR SEQ ID NO:14:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: HUMAN IMMUNODEFICIENY VIRUS
(B) STRAIN: HIV-1

(xi) SEQUENCE DESCRIPTION: SEQ ID NO:14:

Asn Thr Arg Lys Ser Val His Ile Gly Pro Gly Gln Ala Phe Tyr Ala
1 5 10 15

Thr Gly Asp (2) INFORMATION FOR SEQ ID NO:15:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: HUMAN IMMUNODEFICIENY VIRUS
(B) STRAIN: HIV-1

(xi) SEQUENCE DESCRIPTION: SEQ ID NO:15:

Asn Thr Arg Lys Ser Ile His Ile Gly Pro Gly Arg Ala Phe Tyr Thr
1 5 10 15

Thr Gly Glu (2) INFORMATION FOR SEQ ID NO:16:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: HUMAN IMMUNODEFICIENY VIRUS
(B) STRAIN: HIV-1

(xi) SEQUENCE DESCRIPTION: SEQ ID NO:16:

Asn Thr Arg Lys Ser Ile Arg Ile Gly Pro Gly Gln Thr Phe Tyr Ala
1 5 10 15

Thr Gly Glu (2) INFORMATION FOR SEQ ID NO:17:

(i) SEQUENCE CHARACTERISTICS:
(A) LENGTH: 18 amino acids
(B) TYPE: amino acid

-continued ( C ) STRANDEDNESS: single
( D ) TOPOLOGY: linear ( i i ) MOLECULE TYPE: peptide ( v i ) ORIGINAL SOURCE:
( A ) ORGANISM: HUMAN IMMUNODEFICIENY VIRUS
( B ) STRAIN: HIV-1

( x i ) SEQUENCE DESCRIPTION: SEQ ID NO:17:

Asn Thr Arg Gln Arg Thr His Ile Gly Pro Gly Gln Ala Leu Tyr Thr
1 5 10 15

Thr Arg ( 2 ) INFORMATION FOR SEQ ID NO:18:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: HUMAN IMMUNODEFICIENY VIRUS
( B ) STRAIN: HIV-1

( x i ) SEQUENCE DESCRIPTION: SEQ ID NO:18:

Asn Thr Arg Thr Ser Ile Thr Ile Gly Pro Gly Gln Val Phe Tyr Arg
1 5 10 15

Thr Gly Asp ( 2 ) INFORMATION FOR SEQ ID NO:19:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = “SYNTHETIC DNA”

( x i ) SEQUENCE DESCRIPTION: SEQ ID NO:19:

AAATTCCCCT CCACAATTAA AACTG 25

( 2 ) INFORMATION FOR SEQ ID NO:20:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = “SYNTHETIC DNA”

( x i ) SEQUENCE DESCRIPTION: SEQ ID NO:20:

GCCGGATCCT CAACTCAACT GCTGTTAAAT 30

( 2 ) INFORMATION FOR SEQ ID NO:21:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: other nucleic acid ( A ) DESCRIPTION: /desc = "SYNTHETIC DNA"

( x i ) SEQUENCE DESCRIPTION: SEQ ID NO:21:

GCTCTGCAGT CAAATTTCTG GGTCCCCTCC TGAGG 35

( 2 ) INFORMATION FOR SEQ ID NO:22:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: HUMAN IMMUNODEFICIENCY VIRUS
( B ) STRAIN: HIV-1

( x i ) SEQUENCE DESCRIPTION: SEQ ID NO:22:

Asn Thr Arg Lys Ser Ile His Leu Gly Pro Gly Gln Ala Trp Tyr Thr
1 5 10 15

Thr Gly Gln ( 2 ) INFORMATION FOR SEQ ID NO:23:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: HUMAN IMMUNODEFICIENCY VIRUS
( B ) STRAIN: HIV-1

( x i ) SEQUENCE DESCRIPTION: SEQ ID NO:23:

Glu Leu Asp Lys Trp Ala
1 5

( 2 ) INFORMATION FOR SEQ ID NO:24:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:24:

TCGAGTGAGC TGGACAAGTG GGCT 24

( 2 ) INFORMATION FOR SEQ ID NO:25:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:25:

TCGAAGCCCA CTTGTCCAGC TCAC 24

-continued ( 2 ) INFORMATION FOR SEQ ID NO:26:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:26:

T C G A G T A A G A  A C G A G C A G G A  G C T G C T G G A G  C T G G A C A A G T  G G G C T  4 5

( 2 ) INFORMATION FOR SEQ ID NO:27:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:27:

T C G A A G C C C A  C T T G T C C A G C  T C C A G C A G C T  C C T G C T C G T T  C T T A C  4 5

What is claimed is:

1. An immunogenic composition comprising *Mycobacterium bovis* BCG which secretes a fusion protein, wherein the fusion protein is an α-antigen of mycobacteria into which a foreign antigenic peptide has been inserted between adjacent amino acids in a region between position 184 to 203 of the amino acid sequence of the α-antigen.

2. The immunogenic composition of claim 1, wherein the foreign antigenic peptide is inserted between residues 184 and 185 of the amino acid sequence of the α-antigen.

3. The immunogenic composition of claim 2, wherein residue 184 is Ser and residue 185 is Asp.

4. The immunogenic composition of claim 1, wherein the α-antigen is the α-antigen of *Mycobacterium kansasii*.

5. The immunogenic composition of claim 1, wherein the foreign antigenic peptide has a length of at most 19 amino acid residues.

6. The immunogenic composition of claim 1, wherein the foreign antigenic peptide is inserted into the molecular surface of the α-antigen.

7. The immunogenic composition of claim 1, wherein the foreign antigenic peptide is an antigenic peptide of an HIV-1 surface antigen.

8. The immunogenic composition of claim 7, wherein the foreign antigenic peptide comprises the third variable region of HIV-1.

9. The immunogenic composition of claim 8, wherein the foreign antigenic peptide has the amino acid sequence of SEQ ID NO: 1.

10. The immunogenic composition of claim 8, wherein the foreign antigenic peptide has the amino acid sequence of SEQ ID NO: 14, 15, 16, 17 or 18.

11. The immunogenic composition of claim 8, wherein the foreign antigenic peptide has the amino acid sequence of SEQ ID NO: 13.

12. A method of inducing an immune response, comprising administering an amount of the immunogenic composition of claim 1 to a patient effective for inducing an immune response.

13. A method of inducing an immune response, comprising administering an amount of the immunogenic composition of claim 7 to a patient effective for inducing an immune response.

14. A method of inducing antibody production, comprising administering an amount of the immunogenic composition of claim 1 to a patient effective for inducing antibody production.

15. A method of inducing cytotoxic T lymphocytes, comprising administering an amount of the immunogenic composition of claim 1 to a patient effective for inducing cytotoxic T lymphocytes.

16. A method of producing the immunogenic composition of claim 1, comprising transforming *Mycobacterium bovis* BCG with a DNA sequence encoding a fusion protein, wherein the fusion protein is an α-antigen of a mycobacteria into which a foreign antigenic peptide has been inserted between adjacent amino acids in a region between position 184 to 203 of the amino acid sequence of the α-antigen.

* * * * *

UNITED STATES PATENT AND TRADEMARK OFFICE

CERTIFICATE OF CORRECTION

PATENT NO. : 5,858,369

DATED : January 12, 1999

INVENTOR(S) : Kazuhiro MATSUO, et al.

It is certified that error appears in the above-identified patent and that said Letters Patent is hereby corrected as shown below:

On the title page and at the top of Column 1, Item [54], the title, should read:

--ANTI-AIDS SECRETORY RECOMBINANT BCG VACCINE--

Signed and Sealed this

Seventh Day of September, 1999

Attest:

Q. TODD DICKINSON

Attesting Officer

*Acting Commissioner of Patents and Trademarks*